United States Patent [19]
Lin et al.

[11] Patent Number: 5,928,872
[45] Date of Patent: Jul. 27, 1999

[54] SUBTRACTIVE HYBRIDIZATION WITH COVALENTLY BINDING HOMOLOGY

[76] Inventors: Shi-Lung Lin, 731 S. Chapel Ave., Apt. F, Alhambra, Calif. 91801; Shao-Yao Ying, 1953 Wellesley Rd., San Marino, Calif. 91108

[21] Appl. No.: 08/927,859

[22] Filed: Sep. 11, 1997

Related U.S. Application Data

[63] Continuation-in-part of application No. 08/854,400, May 12, 1997.
[51] Int. Cl.$^6$ .............................. C12Q 1/68; C12P 19/34
[52] U.S. Cl. ............................................... 435/6; 435/91.2
[58] Field of Search ................................ 435/6, 91.2, 810

[56] References Cited

U.S. PATENT DOCUMENTS 5,525,471   6/1996   Zeng .
5,589,339   12/1996  Hampson .
5,591,575   1/1997   Hampson .

OTHER PUBLICATIONS

Hampson et al., Nucleic Acids Res. 20(11), 2899 (1992).
Bjourson et al., "Combined Subtraction Hybridization . . . Sequences", *Applied and Environmental Microbiology* 58:2296–2301 (1992).
Chang et al., "Cloning and Expression of a Gamma–Inferoninducible Gene . . . " *International Immunology*; 1–388–397 (1989).
Coochini et al., "Identification of Genes . . . " *Nucleic Acids Res.* 5742–5747 (1993).
Davis et al., "Expression of a SIngle Transfected cDNA . . . " *Cell* 51:987–1000 (1987).
Duguid et al., "Library Subtraction . . . ", *Nucleic Acids Res.* 18:2789–2792(1990).
Kunkel et al., "Specific Cloning . . . " *Proc. Natl Acad. Sci USA* 82,4778–4782 (1985).
Lamar et al. *Cell* 37: 171–177 (1984).
Lehninger et al., "Principles of Biochemistry . . . ", Worth Press, pp. 342–343 (1993).
Lisitsyn et al., "Cloning the Differences . . . " *Science* 259:946–951 (1993).
Littman et al., "The Isolation and Sequence of the Gene . . . " *Cell* 40: 237–246 (1985).
Maddon et al., "The Isolation and Nucleotide . . . " *Cell* 42:93–104 (1985).
Nussbaum et al., *Proc. Natl Acad. Sci* USA 84:6521–6525 (1987).
Sambrook et al, "*Molecular Cloning, 2nd Ed.*", Cold Spring Harbor Laboratory Press, p10.45 (1989).
Straus et al., "Genomic Subtraction . . . " *Proc. Natl Acad. Sci USA* 87:1889–1893 (1990).
Wang et al., "A gene Expression Screen", *Proc. Natl Acad. Sci USA* 88:11505–11509 (1991).
Wicland et al, "A Method for Difference Cloning . . . " *Proc. Natl. Acad. Sci USA* 87:2720–2724 (1990).
Ueli et al., "A Simple and Very Efficient Method . . . " *Gene* 25: pp. 263–269 (1983).

*Primary Examiner*—Kenneth R. Horlick
*Attorney, Agent, or Firm*—Thomas I. Rozsa; Tony D. Chen; Jerry Fong

[57] ABSTRACT

Excess amount of modified subtracter DNA from control cells is generated by carboxylating the base structures of its certain nucleotides with chemical agents in order to introduce covalent affinity between the modified subtracter and a non-modified tester DNA. Hybridization of the control subtracter and the experimental tester DNA is performed with a heat-melting and then cool-reassociation technique. While the desired different (heterologous) sequences remain in the form of hydrogen-binding, common (homologous) sequences of the hybridized DNA are covalently bonded to each other. Since the covalent bonding of the common sequences can not be broken during a polymerase chain reaction, resulting in no amplification of the common sequences but great amplification of the desired different sequences. The desired DNA sequences present after such covalent homologue subtraction and selective amplification represent those DNA sequences which only exist in the tester but not in the subtracter DNA library.

60 Claims, 26 Drawing Sheets

FIG.1(a)

DNA LIBRARY OF
EXPERIMENTAL SET

DNA LIBRARY
OF CONTROL SET

1. AMPLICON DNA GENERATION:
   RESTRICTION-ENDONUCLEASE DIGESTION;
   5'-END ADAPTOR LIGATION.

AMPLICON DNAs OF
EXPERIMENTAL SET
(TESTER)

AMPLICON DNAs
OF CONTROL SET

2. SUBTRACTER N-DNA GENERATION:
   NUCLEOTIDE ANALOG-INCORPORATION PCR

TESTER DNAs OF
EXPERIMENTAL SET

SUBTRACTER U-DNAs
OF CONTROL SET

3. SUBTRACTIVE HYBRIDIZATION:
   MIX OF 1x TESTER TO EXCESS SUBTRACTER,
   MELTING, AND REANNEALING;
   FILLING-THE-3'-ENDS REACTION.

FIG.1(b)

| 4. ABASIC SITE GENERATION: ANALOG-REMOVING ENZYME DIGESTION. |

| 5. DIGESTION OF SURPLUS SUBTRACTER AND HOMOLOGY IN THE ABASIC SITES: NUCLEASE S1 DIGESTION. |

| 6. SELECTIVE AMPLIFICATION: HIGH-ANNEALING-TEMPERATURE PCR |

| 7. DISPLAY OF HETEROLOGOUS DNA RESULTS: ELECTROPHORESIS ON GEL. |

DIFFERENT DNAs PRESENT IN THE EXPERIMENTAL SET, BUT ALMOST ABSENT IN THE CONTROL SET

| 8. VERIFICATION OF THE RESULTS: NORTHERN BLOTTING ASSAY; CLONING; AND SEQUENCING. |

FIG.2(b)

TESTER-HOMOHYBRIDS:     TESTER-SUBTRACTER     SURPLUS SUBTRACTERS
HETEROLOGOUS DNAs     HETEROHYBRIDS:
    HOMOLOGOUS DNAs

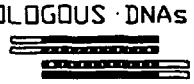
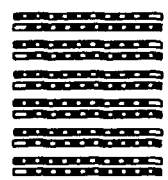

4. ANALOG-REMOVING ENZYME DIGESTION
5. NUCLEASE S1 DIGESTION:

DIFFERENT DNAs
FROM TESTERS     ELIMINATED HOMOLOGY     ELIMINATED SUBTRACTERS

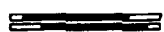

6. SELECTIVE AMPLIFICATION:

T-PRIMER —     HIGH-ANNEALING-TEMPERATURE
POLYMERASE CHAIN REACTION

HETEROLOGOUS DNAs

NO AMPLIFICATION     NO AMPLIFICATION

EXPONENTIAL
AMPLIFICATION

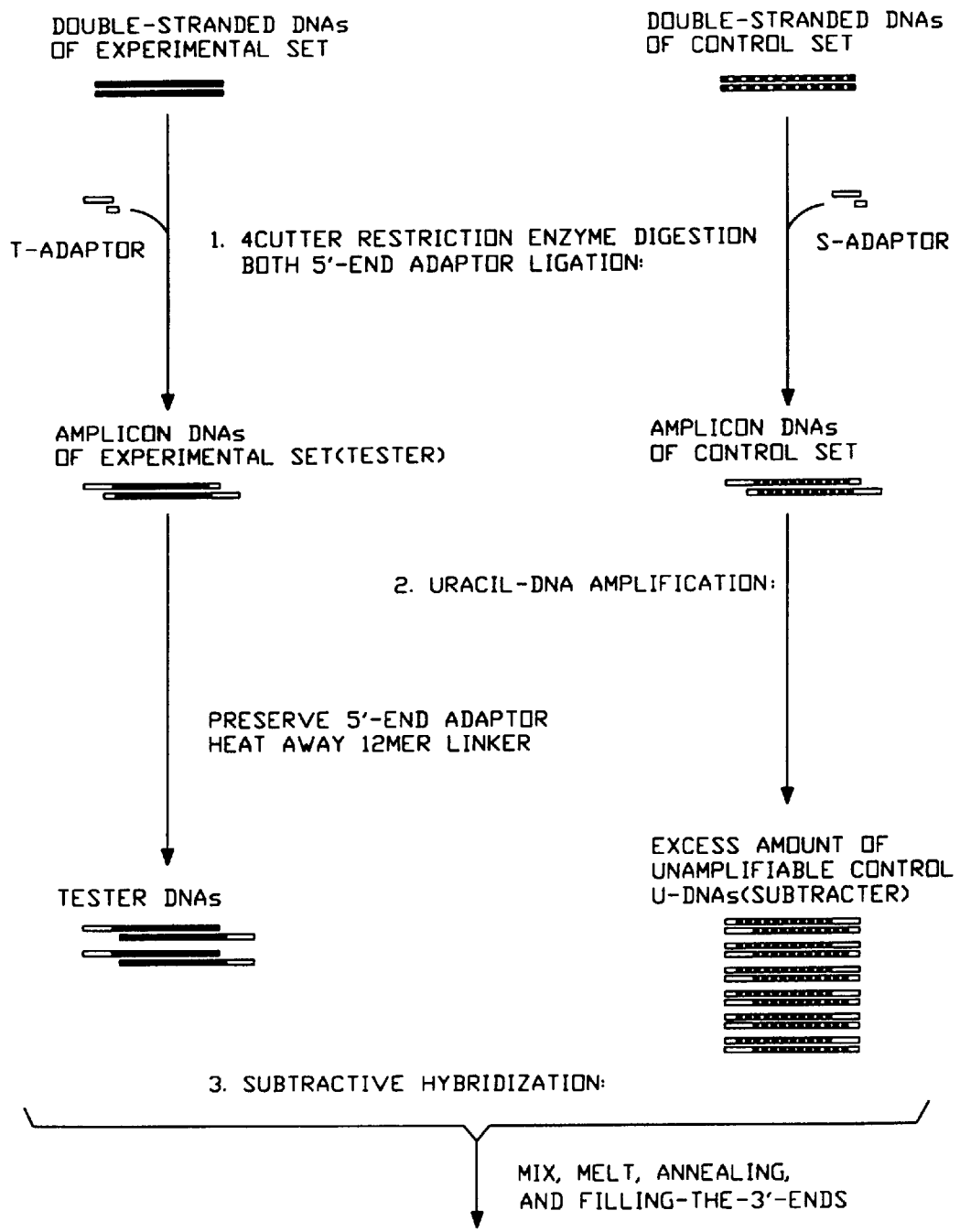

FIG.3(b)

TESTER-HOMOHYBRIDS: HETEROLOGOUS DNAs 

TESTER-SUBTRACTER HETEROHYBRIDS: HOMOLOGOUS DNAs 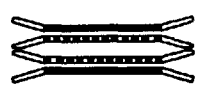

SURPLUS SUBTRACTERS 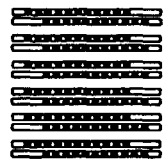

4. URACIL-DNA GLYCOSYLASE DIGESTION:
5. NUCLEASE S1 DIGESTION:

DIFFERENT DNAs FROM TESTERS 

ELIMINATED HOMOLOGY

ELIMINATED SUBTRACTERS

6. SELECTIVE AMPLIFICATION:

T-PRIMER —

HIGH-ANNEALING-TEMPERATURE POLYMERASE CHAIN REACTION

HETEROLOGOUS DNAs 

NO AMPLIFICATION

NO AMPLIFICATION

EXPONENTIAL AMPLIFICATION

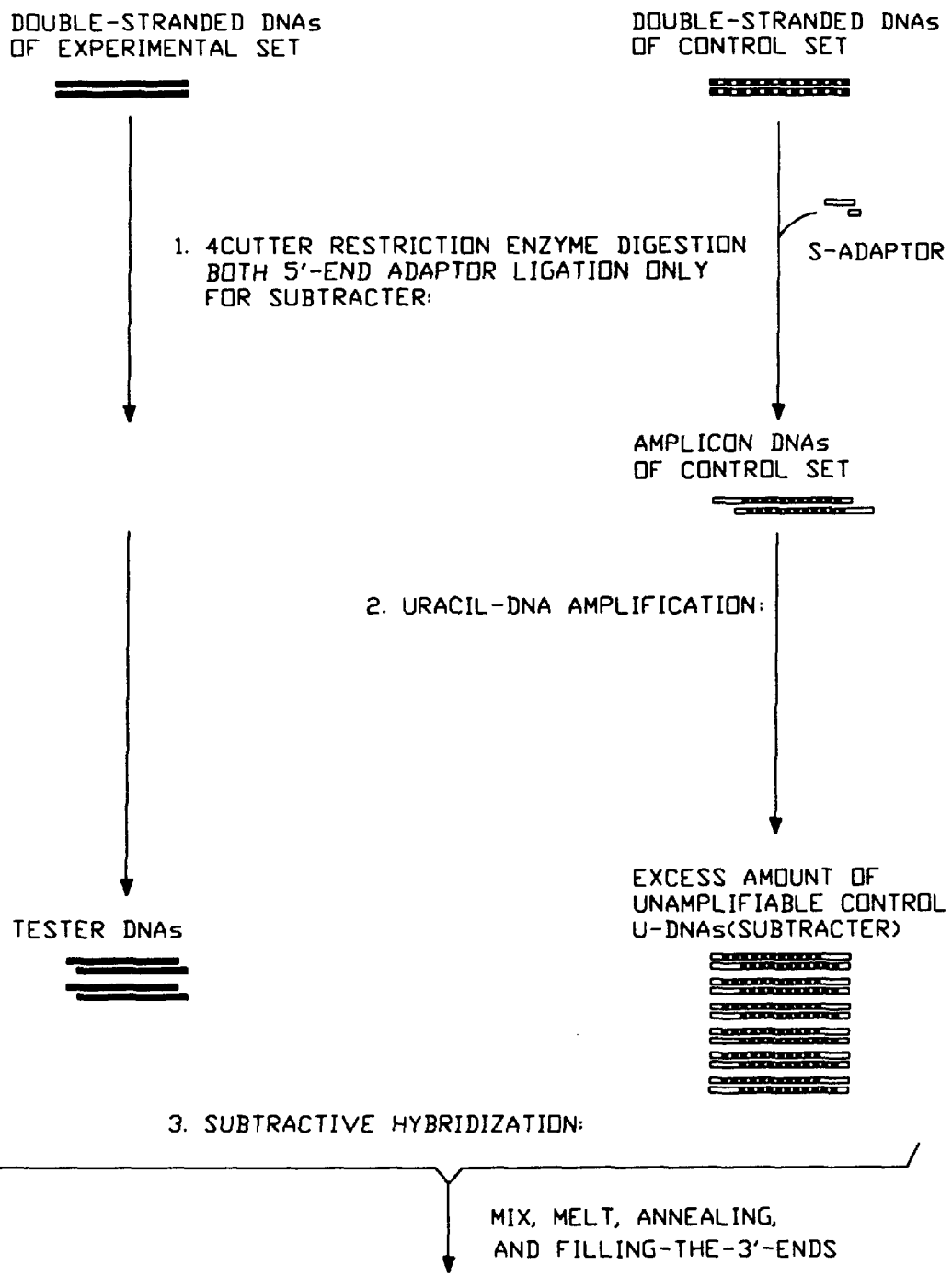
FIG.4(a) WHEN TESTER DNA IS ABUNDANT:

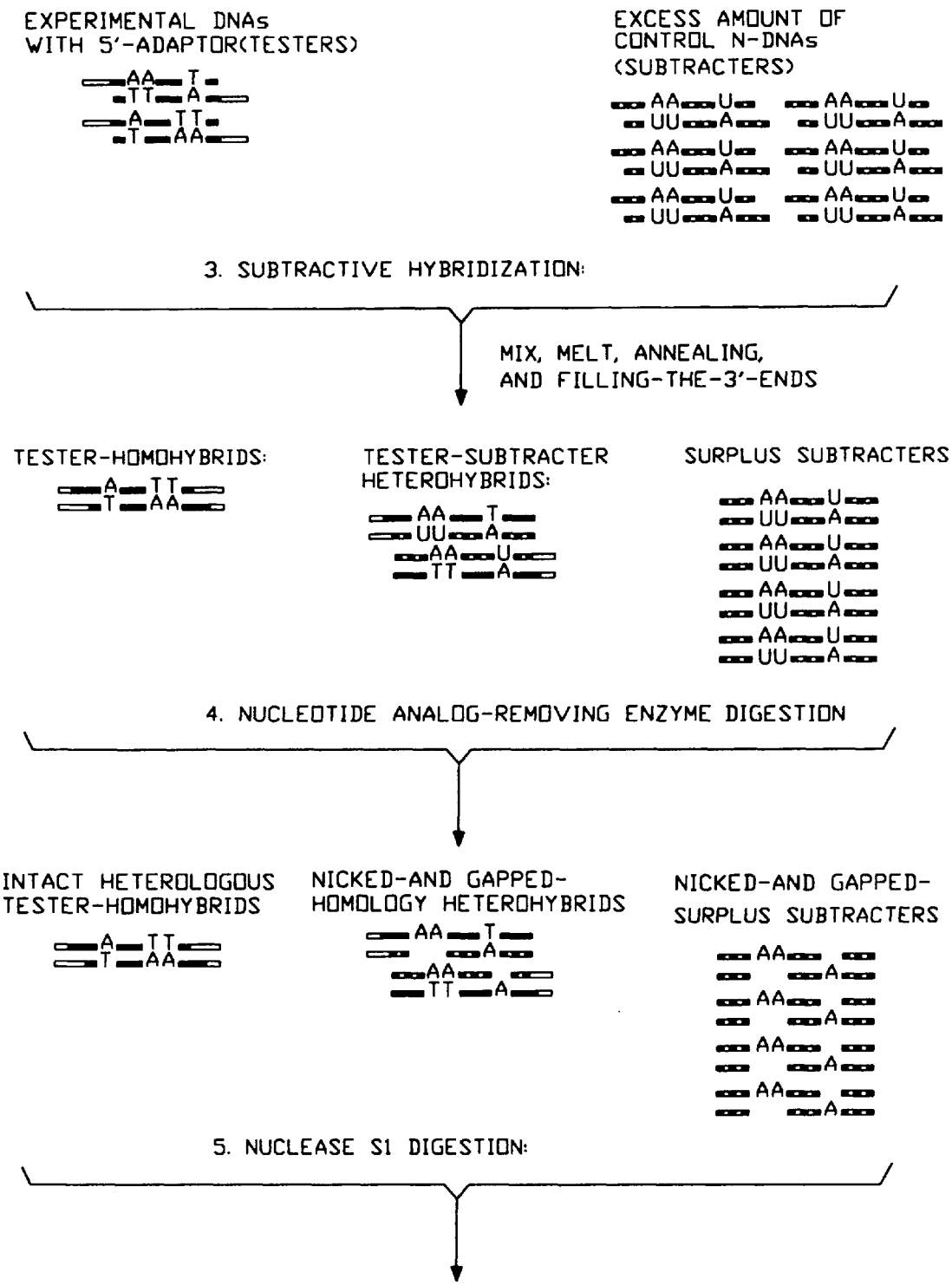

FIG.5(b)

| INTACT HETEROLOGOUS DNAs FROM TESTERS | NICK/GAP-DIGESTED HOMOLOGY FRAGMENTS | NICK/GAP-DIGESTED SUBTRACTER FRAGMENTS |
|---|---|---|
|  |  | 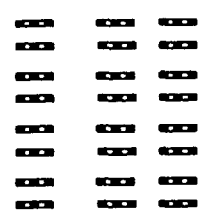 |

6. SELECTIVE AMPLIFICATION:

SPECIFIC TESTER-PRIMER ⊂⊃    HIGH-ANNEALING-TEMPERATURE POLYMERASE CHAIN REACTION

| HETEROLOGOUS DNAs | HOMOLOGOUS DNAs (COMMON SEQUENCES) | SURPLUS SUBTRACTERS |
|---|---|---|
| 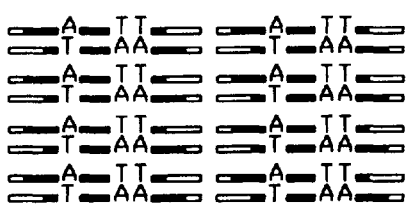 | NO AMPLIFICATION | NO AMPLIFICATION |

EXPONENTIAL AMPLIFICATION cDNA amplicon 108 bp

FIG.7  TABLE 1

| NAME | APPLICATION | SEQUENCE |
|---|---|---|
| 9. T-DPN2-24MER (SEQ ID NO. 1) | 5'-LIGATION ADAPTOR; PCR SPECIFIC PRIMER FOR TESTER GENOMIC DNA. | 5'-GCCACCAGAAGAGCGTGTACGCCA-3' |
| 10. T-DPN2-12MER (SEQ ID NO. 2) | 5'-LIGATION LINKER FOR TESTER GENOMIC DNA. | 5'-GATCTGGCGTAC-3' (5'-DEPHOSPHORYLATED) |
| 11. S-DPN2-24MER (SEQ ID NO. 3) | 5'-LIGATION ADAPTOR; PCR SPECIFIC PRIMER FOR SUBTRACTER GENOMIC DNA. | 5'-CGGUAGUGACUCGGUUAAGAUCGA-3' |
| 12. S-DPN2-12MER (SEQ ID NO. 4) | 5'-LIGATION LINKER FOR SUBTRACTER GENOMIC DNA. | 5'-GAUCUCGAUCUU-3' (5'-DEPHOSPHORYLATED) |
| 13. T-HPA2-24MER (SEQ ID NO. 5) | 5'-LIGATION ADAPTOR; PCR SPECIFIC PRIMER FOR TESTER cDNA. | 5'-GCCACCAGAAGAGCGTGTACGTCC-3' |
| 14. T-HPA2-11MER (SEQ ID NO. 6) | 5'-LIGATION LINKER FOR TESTER cDNA. | 5'-CGGGACGTACA-3' (5'-DEPHOSPHORYLATED) |
| 15. S-HPA2-24MER (SEQ ID NO. 7) | 5'-LIGATION ADAPTOR; PCR SPECIFIC PRIMER FOR SUBTRACTER cDNA. | 5'-CGGUAGUGACUCGGUUAAGAUCGC-3' |
| 16. S-HPA2-11MER (SEQ ID NO. 8) | 5'-LIGATION LINKER FOR SUBTRACTER cDNA. | 5'-CGGCGAUCUUA-3' (5'-DEPHOSPHORYLATED) |

FIG. 8(b)

NON-MODIFIED　　　　　　　COVALENCE-MODIFIED
TESTER DNA　　　　　　　　SUBTRACTER DNA

⇩

4. SUBTRACTIVE HYBRIDIZATION:
   MIX OF 1× TESTER TO EXCESS SUBTRACTER,
   MELTING, AND REANNEALING.

⇩

5. TESTER-SPECIFIC AMPLIFICATION:
   SPECIAL CHS-PCR.

⇩

6. DISPLAY OF HETEROLOGOUS DNA RESULTS:
   ELECTROPHORESIS ON GEL.

⇩

DIFFERENT DNAs PRESENT IN THE
EXPERIMENTAL SET, BUT ALMOST
ABSENT IN THE CONTROL SET

⇩

7. VERIFICATION OF THE RESULTS:
   NORTHERN BLOTTING ASSAY; CLONING; AND
   SEQUENCING.

108bp deletion

FIG.12  TABLE 2

| NAME | APPLICATION | SEQUENCE |
|---|---|---|
| 9. T-DPN2-24MER (SEQ ID NO. 1) | 5'-LIGATION ADAPTOR; PCR SPECIFIC PRIMER FOR TESTER GENOMIC DNA. | 5'-GCCACCAGAAGAGCGTGTACGCCA-3' |
| 10. T-DPN2-12MER (SEQ ID NO. 2) | 5'-LIGATION LINKER FOR TESTER GENOMIC DNA. | 5'-GATCTGGCGTAC-3' (5'-DEPHOSPHORYLATED) |
| 11. S-DPN2-24MER (SEQ ID NO. 3) | 5'-LIGATION ADAPTOR; PCR SPECIFIC PRIMER FOR SUBTRACTER GENOMIC DNA. | 5'-CGGUAGUGACUCGGUUAAGAUCGA-3' |
| 12. S-DPN2-12MER (SEQ ID NO. 4) | 5'-LIGATION LINKER FOR SUBTRACTER GENOMIC DNA. | 5'-GAUCUCGAUCUU-3' (5'-DEPHOSPHORYLATED) |
| 13. T-HPA2-24MER (SEQ ID NO. 5) | 5'-LIGATION ADAPTOR; PCR SPECIFIC PRIMER FOR TESTER cDNA. | 5'-GCCACCAGAAGAGCGTGTACGTCC-3' |
| 14. T-HPA2-11MER (SEQ ID NO. 6) | 5'-LIGATION LINKER FOR TESTER cDNA. | 5'-CGGGACGTACA-3' (5'-DEPHOSPHORYLATED) |
| 15. S-HPA2-24MER (SEQ ID NO. 7) | 5'-LIGATION ADAPTOR; PCR SPECIFIC PRIMER FOR SUBTRACTER cDNA. | 5'-CGGUAGUGACUCGGUUAAGAUCGC-3' |
| 16. S-HPA2-11MER (SEQ ID NO. 8) | 5'-LIGATION LINKER FOR SUBTRACTER cDNA. | 5'-CGGCGAUCUUA-3' (5'-DEPHOSPHORYLATED) |

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic DNA"

(xi) SEQUENCE DESCRIPTION: SEQ ID NO:1:

GCCACCAGAA GAGCGTGTAC GCCA                                               24

(2) INFORMATION FOR SEQ ID NO:2:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic DNA"

(xi) SEQUENCE DESCRIPTION: SEQ ID NO:2:

```
GATCTGGCGT AC                                                          12
```

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:3:

```
CGGTAGTGAC TCGGTTAAGA TCGA                                             24
```

(2) INFORMATION FOR SEQ ID NO:4:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:4:

```
GATCTCGATC TT                                                          12
```

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:5:

```
GCCACCAGAA GAGCGTGTAC GTCC                                             24
```

(2) INFORMATION FOR SEQ ID NO:6:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:6:

```
CGGGACGTAC A                                                           11
```

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:7:

```
CGGTAGTGAC TCGGTTAAGA TCGC                                              24
```

(2) INFORMATION FOR SEQ ID NO:8:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:8:

```
CGGCGATCTT A                                                            11
```

SUBTRACTIVE HYBRIDIZATION WITH COVALENTLY BINDING HOMOLOGY

The present application is a continuation-in-part of application Ser. No. 08/854,400 filed May 12, 1997.

BACKGROUND OF THE INVENTION

1. Field of the Invention

The present invention generally relates to the field of methods for isolating specific nucleotide sequences. More particularly, the present invention relates to the field of improved methods of rapid isolation of differentially expressed genes or deleted/inserted sequences in genome DNA through subtractive hybridization with covalently-binding homology and selective amplification.

2. Description of the Prior Art

The following references are pertinent to this invention:

1. Bjourson et. al., "Combined Subtraction Hybridization and Polymerase Chain Reaction Amplification Procedure for Isolation of Strain-specific Rhizobium DNA Sequences", *Applied and Environmental Microbiology* 58: 2296–2301 (1992)
2. Chang et. al., "Cloning and Expression of a Gamma-interferon-inducible Gene in Monocytes: a New Member of a Cytokine Gene Family", *International Immunology* 1:388–397 (1989).
3. Coochini et. al., "Identification of Genes Up-regulated in Differentiating Nicotania glauca Pith Tissue, Using an Improved Method for Construction a Subtractive cDNA Library", *Nucleic Acids Res.* 21: 5742–5747 (1993).
4. Davis et. al., "Expression of a Single Transfected cDNA Converts Fibroblasts to Myoblasts", *Cell* 51: 987–1000 (1987).
5. Duguid et. al., "Library Subtraction of In Vitro cDNA Libraries to Identify Differentially Expressed Genes in Scapic Infection", *Nucleic Acids Res.* 18: 2789–2792 (1990).
6. Kunkel et. al., "Specific Cloning of DNA Fragments Absent from the DNA of a Male Patient with an X Chromosome Deletion", *Proc. Natl. Acad. Sci. USA* 82, 4778–4782 (1985).
7. Lamar et. al., "Y-encoded, Species-specific DNA in Mice: Evidence That the Y Chromosome Exists in Two Polymorphic Forms in Inbred Strains", *Cell* 37:171–177 (1984).
8. Lehninger et. al., *"Principles of Biochemistry, 2nd Edition"*, Worth Press, pp342–343 (1993).
9. Lisitsyn et. al., "Clonning the Differences Between Two Complex Genomes", *Science* 259: 946–951(1993).
10. Littman et. al., "The Isolation and Sequence of the Gene Encoding T8: a Molecule Defining Functional Classes of T Lymphocytes", *Cell* 40: 237–246 (1985).
11. Maddon et. al., "The Isolation and Nucleotide Sequence of a cDNA Encoding the T Cell Surface Protein T4: a New Member of the Immunoglobulin Gene Family", *Cell* 42: 93–104(1985).
12. Nussbaum et. al., "Isolation of Anonymous DNA Sequences from within a Submicroscopic X Chromosomal Deletion in a Patient with Choroideremia, Deafness, and Mental Retardation", *Proc. Natl. Acad. Sci. USA* 84: 6521–6525 (1987).
13. Sambrook et. al., *"Molecular Cloning, 2nd Edition"*, Cold Spring Harbor Laboratory Press, p10.45 (1989).
14. Solomons et. al., *"Organic Chemistry, 6th Edition"*, John Wiley & Sons Press, pp 693, 803–804 (1996).
15. Straus et. al., "Genomic Subtraction for Cloning DNA Corresponding to Deletion Mutations", *Proc. Natl. Acad. Sci. USA* 87: 1889–1893 (1990).
16. Wang et. al., "A Gene Expression Screen", *Proc. Natl. Acad. Sci. USA* 88: 11505–11509 (199 1).
17. Wicland et. al., "A Method for Difference Cloning; Gene Amplification Following Subtractive Hybridization", *Proc. Natl. Acad. Sci. USA* 87: 2720–2724 (1990).
18. Ueli et. al., "A Simple and Very Efficient Method for Generating cDNA Libraries", *Gene*, 25: pp263–269 (1983).
19. U.S. Pat. No. 5,525,471 issued to Zeng Jin on Jun. 11, 1996 for "Enzymatic Degrading Subtraction Hybridization".
20. U.S. Pat. No. 5,589,339 issued to Hampson et al. on Dec. 31, 1996 for "Subtraction Hybridization".
21. U.S. Pat. No. 5,591,575 issued to Hampson et al. On Jan. 7, 1997 for "Subtraction Hybridization Employing Aziridinyl Benoquinone Cross-Linking Agents".

The ability to compare two different DNA libraries has permitted inquiries into the role of differentially expressed genes or deleted-/inserted-genomic sequences involving the mechanisms of neoplastic transformation, developmental regulation, therapeutic effect, pathological disorder, and cell-physiological phenomena. Understanding the alterations of gene expression and chromosomal rearrangement between normal and disordered cells is especially important for gene therapy, eugenical improvement, pharmaceutical design and etiological investigation.

Several methods have been designed to detect and isolate different DNA sequences which are present in one DNA library but absent in another one. One of the most commonly used methods to accomplish such purpose is subtractive hybridization, involving the elimination of homologous (common) sequences from the mixture of two mutually compared DNA libraries. This kind of selective isolation can be done either between two cDNA libraries (Davis et. al., *Cell* 51: 987–1000 (1987)), or between two genomic DNA libraries (Lamar et. al., *Cell* 37: 171–177 (1984)). In brief, this method relies upon the generation of double-stranded DNA libraries from both control cells (subtracter DNA) and cells after experiment, treatment, disorder or change (tester DNA). The two DNA libraries are then denatured and hybridized to each other, resulting in subtracter-tester duplex formation if a sequence is common to both DNA populations. By removing the subtracter and common sequences, the remaining DNA is the desired different sequence which is only present in the tester and also highly related to the treatment, disorder or change of interest.

Subtractive hybridization has been successfully used in the discovery of many functional genes and crucial genomic loci, such as $T_4$ & $T_8$ lymphocyte-surface glycoproteins (Maddon et. al., *Cell* 42: 93–104 (1985); Littnan et. al., *Cell* 40: 237–246 (1985)), gamma-interferon-induced cytokines in monocytes (Chang et. al., *International Immunology* 1:388–397 (1989)), choroidermia loci (Nussbaum et. al., *Proc. Natl. Acad. Sci. USA* 84: 6521–6525 (1987)), Duchenne muscular dystrophy-related loci (Kunkel et. al., *Proc. Natl. Acad. Sci. USA* 82, 4778–4782 (1985)), and human Y-chromosome-specific DNA (Lamar, 1984).

In some cases, the isolated desired DNA is so abundant in a cell source that it can be detected directly without prior enrichment. In most cases, however, the small amount of desired DNA requires that it be amplified by a polymerase-chain-reaction (PCR), which allows a strengthened observation after subtractive hybridization (Wang et. al., *Proc. Natl. Acad. Sci. USA* 88: 11505–11509 (1991); Coochini et. al., *Nucleic Acids Res.* 21: 5742–5747 (1993)). Additionally, PCR amplification can be used to enrich both subtracter and tester libraries when starting material is limited (Wicland et.

al., *Proc. Natl. Acad Sci. USA* 87: 2720–2724 (1990)). In short, such amplification is achieved by ligating a specific adaptor to the both ends of an endonuclease-restricted DNA library (amplicon DNA), resulting in the generation of a primer-conjugated region for PCR amplification. However, the PCR amplification may also cause non-specific subtracter contamination when a multiple subtraction and amplification procedure is applied.

Using biotinylated subtracter DNAs has been widely adopted to increase the specificity of subtraction with streptavidin-containing chromatography and to reduce the amount of subtracter needed for hybridization. Straus et. al. (*Proc. Natl. Acad. Sci. USA* 87: 1889–1893 (1990)) used biotinylated-deletion-mutant genomic DNAs to hybridize with restricted-wild-type genomic DNAs, and then subtracted the unwanted common hybrid-duplexes with avidin-coated beads. The remaining sequences were ligated to a specific adaptor and amplified by PCR, resulting in a finding of genomic deletions present in the mutant but absent in the wild type. Meanwhile, Duguid et. al. (*Nucleic Acids Res.* 18: 2789–2792 (1990)) performed a similar experiment but using a biotinylated double-stranded cDNA library of a normal hamster brain to hybridize with a non-modified cDNA library of a scrapie-infected hamster brain, generating biotinylated hybrid complexes which were removed by a biotin-binding avidin resin. The cDNAs remaining in the suspension were amplified and confirmed as scrapie-infected specific gene sequences. Based on experiments like these, it is noteworthy that most previous methods require several cycles of subtractive hybridization because of the incomplete nature of the biotin-avidin affinity interaction. That means: although these methods can successfully reduce the contamination-potential of the subtracter DNA, the inevitable uses of biotinylation and multiple chromatography cause an increase of tedious laboratory-work and a potential loss of desired sequences during repeated subtraction steps.

Bjourson et. al. (*Applied and Environmental Microbiology* 58: 2296–2301 (1992)) reported a further improvement in subtractive hybridization methods that employed a biotinylated primer and a uracil-containing deoxynucleotide mixture (e.g. mixture of dATP, dCTP, dGTP and dUTP) to generate biotinylated uracil-containing DNA (U-DNA) subtracter in PCR. In this case, control and experimental DNA libraries were isolated from different strains of *Rhizobium leguminosarum*, restricted by an endonuclease, and ligated to different specific adaptors. After that, a special PCR, called uracil-incorporation PCR, was performed to produce the biotinylated subtracter U-DNA which was then hybridized with relatively limited amount of non-modified experimental DNA, resulting in the formation of biotinylated heterohybrid-duplexes that contained homologous sequences common to both libraries. Since the biotinylated hybrids were removed by streptavidin-phenol-chloroform extraction and surplus U-DNA was finally digested with uracil-DNA glycosylase (UDG), the remaining DNA should be the strain-specific sequences; however, this method still required tedious work in biotinylation and at least two rounds of extraction and chromatography.

Prior art attempts at simplifying subtraction with enzymatic digestion, such as U.S. Pat. No. 5,525,471 to Jin, uses a two-exonuclease degradation precedure. Tester cDNA (from experimental cells) is modified by the incorporation of deoxynucleoside thiotriphosphates which protects the tester from digestion by a first exonuclease. After the tester is hybridized with a non-modified subtracter cDNA (from control cells), the surplus subtracter homohybrid and the entire subtracter-half of the tester-subtracter heterohybrid are digested by the first exonuclease. Before the single-stranded tester half of the heterohybrid can reassociate with each other, a second exonuclease digests all single-stranded tester sequences. This can give a quick, simple way to achieve subtractive hybridization, but it also generates some other problems. First, the property of the desired tester sequence is altered by the modifications which may hinder subsequent analysis. Second, a small amount of reassociation of the single-stranded-tester may occur before the second digestion, resulting in an increase of false-positive results. Third, a long-term, two-exonuclease degradation may damage the small amount of desired sequences, resulting in an increase of false-negative results.

Prior art attempts at simplifying subtraction with covalent affinity, such as U.S. Pat. No. 5,589,339 and U.S. Pat. No. 5,591,575 to Hampson, uses an aziridinylbenzoquinone interstrand cross-linking agent to covalently subtract common sequences from tester library. Single-stranded tester is hybridized with single-stranded subtracter (driver) to form hybrid duplexes first, and then the aziridinylbenzoquinone is added to generate covalent bonds between the hybrid duplexes. Because the aziridinylbenzoquinone cross-links all double-stranded sequences, this kind of external covalent-bonding greatly increases the completion of homology subtraction after hybridization. However, during subtractive hybridization only the single-stranded tester and subtracter (driver) can be used as samples in this method due to the interstrand cross-linking nature of the aziridinylbenzoquinone-like agents, resulting in no detection of genomic DNA samples, no detection of limited starting materials and no adaptor-specific amplification of final results. These disadvantages cause more restrictions of sample selection, less stability of sample storage and less sensitivity of final result detection in comparison with a traditional subtraction hybridization of double-stranded DNAs. Also, the determination of final desired sequences is completed by a non-specific random-primer extension reaction which lowers the specificity of final results.

In summary, it is desirable to have a fast, simple, and reliable subtractive hybridization method for distinguishing different sequences from two cDNA or genomic DNA libraries, of which the differences may contribute to developing a therapy for diseases, a diagnosis for inherent problems, or a design for genetic engineering.

SUMMARY OF THE INVENTION

The present invention is a novel subtractive hybridization method which provides a fast, simple, and reliable isolation of desired different sequences from either cDNA or genomic DNA libraries.

Described in detail, a preferred embodiment of the present invention method includes the following steps:
 (a) providing a library of nucleotide analog-containing subtracter DNA which is susceptible to the digestion of a nucleotide analog-removing enzyme;
 (b) contacting the denatured nucleotide analog-containing subtracter DNA with a library of denatured tester DNA which is not affected by the nucleotide analog-removing enzyme, to form a denatured mixture;
 (c) permitting both nucleotide analog-containing subtracter DNA and tester DNA in the denatured mixture under conditions sufficient to form double-stranded hybrid duplexes comprise of homo- and hetero-duplexes;
 (d) digesting the nucleotide analog-containing hybrid DNA with the nucleotide analog-removing enzyme to generate abasic-nicks/gaps in the subtracter homoduplex and the subtracter-tester heteroduplex; and (e) breaking the abasic-nicks/gaps with a single-strand-specific nuclease and thereby provide a library enriched in the library of tester DNA but almost absent in the library of subtracter DNA.

The preferred embodiment of the present invention method additionally may include the pre-steps of forming double-stranded amplicon DNA of the sample, and prior to commencing the aforementioned step (a):

(1) restricting the initial DNA library with a restriction-endonuclease to generate 5'-cohesive termini on both ends;

(2) ligating a specific adaptor to the ends of the restricted DNA where a template is generated for binding with a specific complementary-primer; and (3) incubating the ligated DNA in denatured form with the specific primer under conditions sufficient to permit the template-dependent extension of the primer to thereby enrich the amount of the initial DNA library and also provide an opportunity for incorporating nucleotide analog into the subtracter in the step (a).

In one aspect of the preferred embodiment described above, steps (b)–(e) are repeated on the enriched library at least once. Advantageously, the enriched library can be made from either a cDNA library or a genomic DNA library. In another aspect of this preferred embodiment, the enriched library is amplified, preferably, by PCR in the pre-step (3). To increase subtraction force, the subtracter is preferably generated by incorporation with uridine-nucleotide analog (dU) to raise the bonding efficiency by forming adenine-uracil bonding (as in RNA) which is more stable than traditional adenine-thyerine bonding (as in DNA). Most preferably, the urdine analog is deoxyuridine triphosphate. Advantageously, the nucleotide analog-containing subtracter DNA is susceptible to the digestion of a nucleotide analog-removing enzyme which can remove entire nucleotide analog or its base structure from the nucleotide analog-containing DNA, while the tester DNA is not affected. Preferably, the nucleotide analog-removing enzyme is a uracil-removing enzyme; most preferably, the uracil-DNA glycosylase (UDG).

According to another aspect of this embodiment, the nucleotide analog is incorporated into the subtracter DNA by DNA polymerase. Preferably, the DNA polymerase is Taq polymerase. To prevent the reassociation of undesired tester-sequences during sequentially enzymatic digestion, the nucleotide analog-removing enzyme only generates partially single-stranded duplexes by introducing abasic-nicks/gaps within the tester-subtracter hybrid duplexes after removing the incorporated nucleotide analog or its base structure. Advantageously, the partially single-stranded duplexes are susceptible to the digestion of single-strand-specific nuclease. Preferably, the nuclease is the nuclease S1 or Mung-Bean nuclease. Preferably, the tester DNA and nucleotide analog-containing subtracter DNA have a ratio of between about 1:10 and about 1:150; most preferably, the ratio is 1:50.

The present invention is also a kit for performing subtractive hybridization of cDNA or genomic DNA libraries, comprising individual ones, or any combinations thereof, of the following components:

(a') deoxyuridine triphosphate which confers susceptibility to the digestion of uracil-removing enzyme upon incorporation into a DNA molecule;

(b') a specific tester-adaptor/primer which protects both ends of the tester from the digestion of single-strand-specific nuclease, and also confers amplification-capability to the tester DNA;

(c') a specific subtracter-adaptor/primer which is unprotected from the digestion of uracil-removing enzyme, and confers amplification-capability to the uracil-containing subtracter DNA;

(d') a template-dependent dU-incorporation activity;

(e') a uracil-removing enzyme;

(f') a uracil-removing enzyme buffer;

(g') a single-strand-specific nuclease; and (h') a nuclease buffer.

Preferably, the specific adaptors/primers for tester and subtracter are those shown in Table 1, which is a list of preferred adaptors/primers used in the preferred embodiment of the present invention, and the dU-incorporation activity in (d') is rendered by Taq polymerase. Advantageously, the uracil-removing enzyme is uracil-DNA glycosylase and the single-strand-specific nuclease is nuclease S1.

Alternatively, described in detail, a preferred embodiment of the present invention method includes the following steps:

(a) providing a library of tester DNA which is ligated to a tester-specific adaptor for selective amplification;

(b) contacting the denatured tester DNA with a library of denatured subtracter DNA which is modified by chemical agents in its base structures in order to covalently bond with its tester homologue, to form a denatured mixture;

(c) permitting both tester DNA and subtracter DNA in the denatured mixture under conditions sufficient to form double-stranded hybrid duplexes comprising of hydrogen-bonded homoduplexes and covalently-bonded heteroduplexes; and (d) amplifying the hydrogen-bonded homoduplexes with tester-specific primer and thereby providing a library enriched in the library of tester DNA but almost absent in the library of subtracter DNA.

The preferred embodiment of the present invention method additionally may include the pre-steps of forming double-stranded amplicon DNA of the sample, and prior to commencing the aforementioned step (a):

(1) restricting the initial DNA library with a restriction-endonuclease to generate 5'-cohesive termini on both ends;

(2) ligating a specific adaptor to the ends of the restricted DNA where a template is generated for binding with a specific complementary-primer; and (3) incubating the ligated DNA in denatured form with the specific primer under conditions sufficient to permit the template-dependent extension of the primer to thereby enrich the amount of the initial DNA library.

In one aspect of the preferred embodiment described above, steps (b)–(e) are repeated on the enriched library at least once. Advantageously, the enriched library can be made from either a cDNA library or a genomic DNA library.

According to another aspect of this embodiment, the starting library is amplified, preferably, by PCR in the pre-step (3). To increase subtraction force, the subtracter is preferably carboxylated on the $C_4$ of uracil/thymine or $C_5/C_6$ of pyrimidines in order to raise the bonding stability by forming covalent peptide bonds to the tester's amino-group on the $C_6$ of adenine or $C_6/C_2$ of purines respectively. Most preferably, the carboxylated group is on the $C_5$ of uracil which covalently bond to the $C_6$-amino-group of adenine. Advantageously, the covalent bonds of heterohybrid duplexes can not be broken during amplification in which targeted tester-tester homoduplexes are amplified with a specific adaptor-primer. Preferably, the specific priming amplification is accomplished by PCR-like DNA polymerases. More preferably, the DNA polymerase is Taq/Pwo polymerase. To prevent the reassociation of undesired subtracter-subtracter duplexes during hybridization, the amino-groups of subtracter DNA are blocked or removed by chemical blocking agents. Preferably, the blocking agent is acetic anhydride which converts the subtracter's amino-groups of purines into inactive acetamido-groups. Advantageously, the single-stranded subtracter DNA only covalently hybridizes with the homologous tester DNA, resulting in an increase of subtraction completion and efficiency. Preferably, the tester and subtracter DNA have a ratio of between about 1:1 and about 1:100; most preferably, the ratio is 1:5 to 1:10.

The present invention is also a kit for performing subtractive hybridization of cDNA or genomic DNA libraries, comprising individual ones, or any combinations thereof, of the following components:

(a') a specific tester-adaptor/primer which confers amplification-capability only to the tester DNA;

(b') a specific subtracter-adaptor/primer which confers amplification-capability only to the subtracter DNA;

(c') an amino-blocking agent which prevents the reassociation of the subtracter DNA by blocking hydrogen-bonds and single-stranding;

(d') a carboxylating agent which generates carboxyl-group on the base structures of the subtracter DNA in order to covalently bond with the tester homologue;

(e') a hybridization buffer which permits the tester and subtracter DNA in a denatured mixture to form hydrogen-binded homoduplexes and covalently-bonded heteroduplexes; and (f') a specific amplification activity.

Preferably, the specific adaptors/primers for tester and subtracter are those shown in Table 2, which is a list of preferred adaptors/primers used in the preferred embodiment of the present invention, and the amplification activity in (f') is rendered by Taq/Pwo polymerase. Advantageously, the amino-blocking agent is acetic anhydride or alkaline acetic chloride, and the carboxylating agent is hot alkaline potassium permanganate or sodium cyanide/sulfuric acid mixture.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIGS. 1a–1b is a flowchart of a preferred embodiment of the nucleotide analog-containing hybrid subtraction of the subject invention;

FIGS. 2a–2b is an illustration of the nucleotide analog-containing hybrid subtraction of FIGS. 1a–1b;

FIGS. 3a–3b is an illustration of second preferred embodiment of the nucleotide analog-containing hybrid subtraction of the subject invention;

FIGS. 4a–4b is an illustration of third preferred embodiment of the nucleotide analog-containing hybrid subtraction of the subject invention;

FIGS. 5a–5b is a detailed illustration of the sequentially enzymatic digestion from step 3 to step 6 of FIG. 2b;

FIG. 7 is a table listing the specific adaptors/primers for tester and subtracter utilized in the present invention;

FIGS. 8a–8b is a flowchart of an alternative preferred embodiment of the covalent homologue subtraction hybridization of the subject invention;

FIGS. 10a–10e is a detailed illustration of some of the preferred covalent modifications in the step 3 of FIG. 9a;

FIG. 12 is a table (Table 2) listing the adaptors/primers used in the present invention.

DESCRIPTION OF THE PREFERRED EMBODIMENT

Figure 2A:
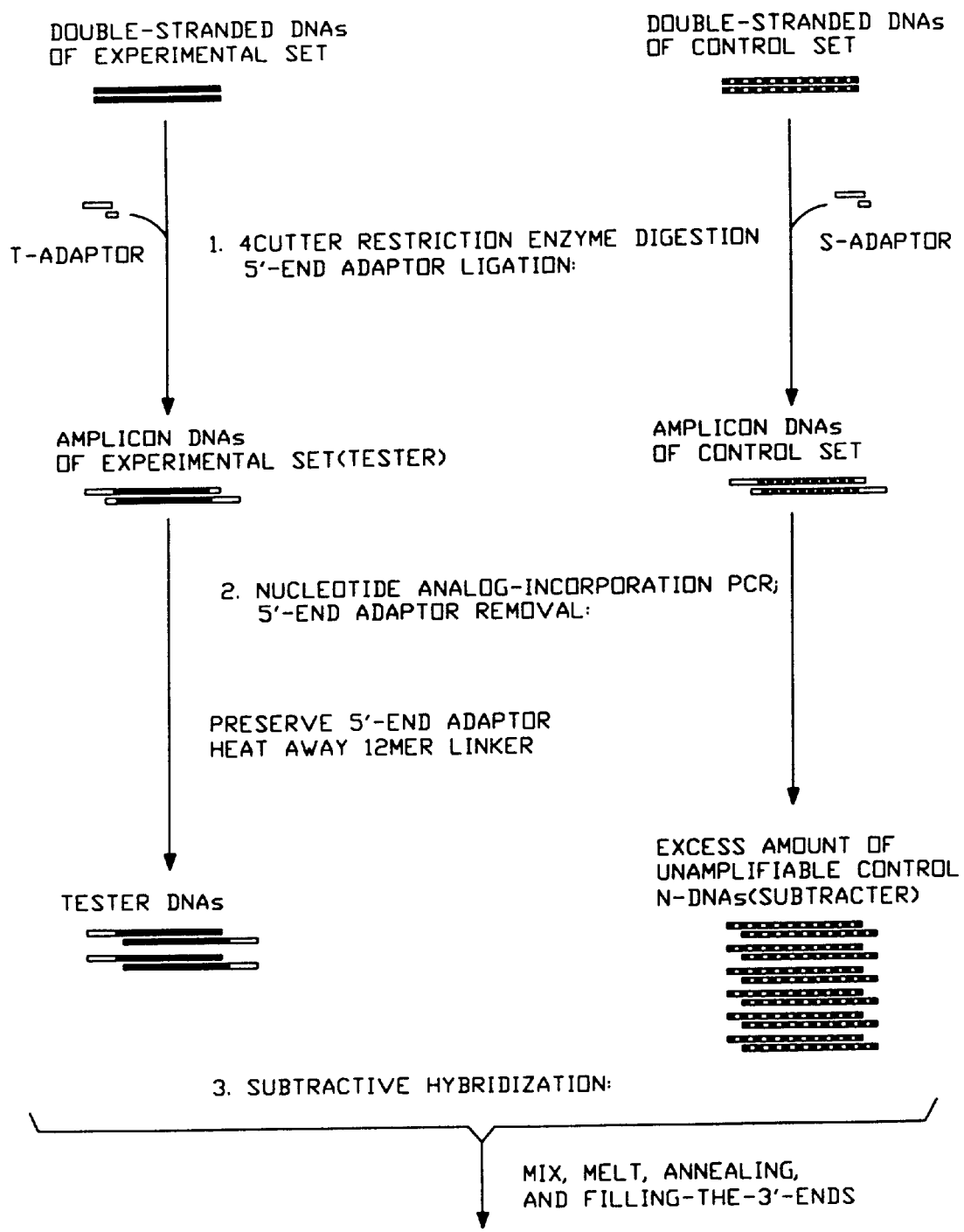

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The present invention is directed to an improved subtractive hybridization method, called nucleotide analog-containing DNA subtraction assay (NDSA), for screening different sequences between two cDNA or genomic DNA libraries. This method is primarily designed for quickly isolating different expression genes (either up- or down-regulated), easily detecting large genomic deletions/insertions, and precisely searching chromosome-specific loci. The preferred version of the present invention is based on: the nucleotide analog-incorporated subtracter hybridization with non-modified tester DNA, the abasic-nick/gap generation in common sequences by a nucleotide analog-removing enzyme, and the abasic-nick/gap cleavage by a single-strand-specific nuclease. In conjunction with an adaptor-ligation and a specific PCR amplification, a very small amount of DNA library can be used as an initial sample for this method.

As used herein, tester DNA refers to the DNA isolated from treated, mutated, infected, differentiated, or abnormal cell source, while subtracter DNA refers to the DNA isolated from a cell source with different status, such as non-treated, un-/further-differentiated, and relatively normal cells (or tissue with nearly homogeneous cells). And, such referring can be done vice versa. The tester DNA library contains desired sequences which are abundant in the tester but very limited in the subtracter. The desired sequences represent the differences of gene expression (if a cDNA library is used), or those of genomic complexity (if a genomic DNA library is used). The isolation of the desired sequences is achieved herein by using a nucleotide analog-incorporated subtracter DNA (subtracter N-DNA) to remove common sequences through hybridization and sequentially enzymatic digestion, which is referred to the digestion of nucleotide analog-removing enzyme and single-strand-specific nuclease. The nucleotide analog-removing enzyme refers to the enzyme which can generate nicks or gaps by removing nucleotide analog or its base structure from double-stranded DNA. The common sequence refers to the sequence which is common to both tester- and subtracter-DNA populations.

The advantages of using nucleotide analog-containing subtracter DNA are as follows: First, during subtractive hybridization, the affinity of subtracter to homologous tester can be greatly enhanced by the nucleotide analog-incorporation, such as dU-incorporation which renders a RNA-like character to the subtracter to increase the stability of bonding with tester DNA (Lehninger et. al., "*Principles of Biochemistry*, 2nd Edition", pp342–343). This stronger bonding between subtracter and tester accomplishes the completion of homology subtraction. Second, the digestion of nucleotide analog-removing enzyme eliminates all undesired nucleotide analog-containing DNA structure, resulting in a very low background from non-specific subtracter contamination. Third, because the digestion of nucleotide analog-removing enzyme only removes nucleotide analog or its base structure from the subtracter-part of hybrids, this partially-digested subtracter maintains the tester-subtracter hybrids in a partially single-stranded conformation which contains nicks and gaps for digestion by a single-strand-specific nuclease.

Figure 4B:
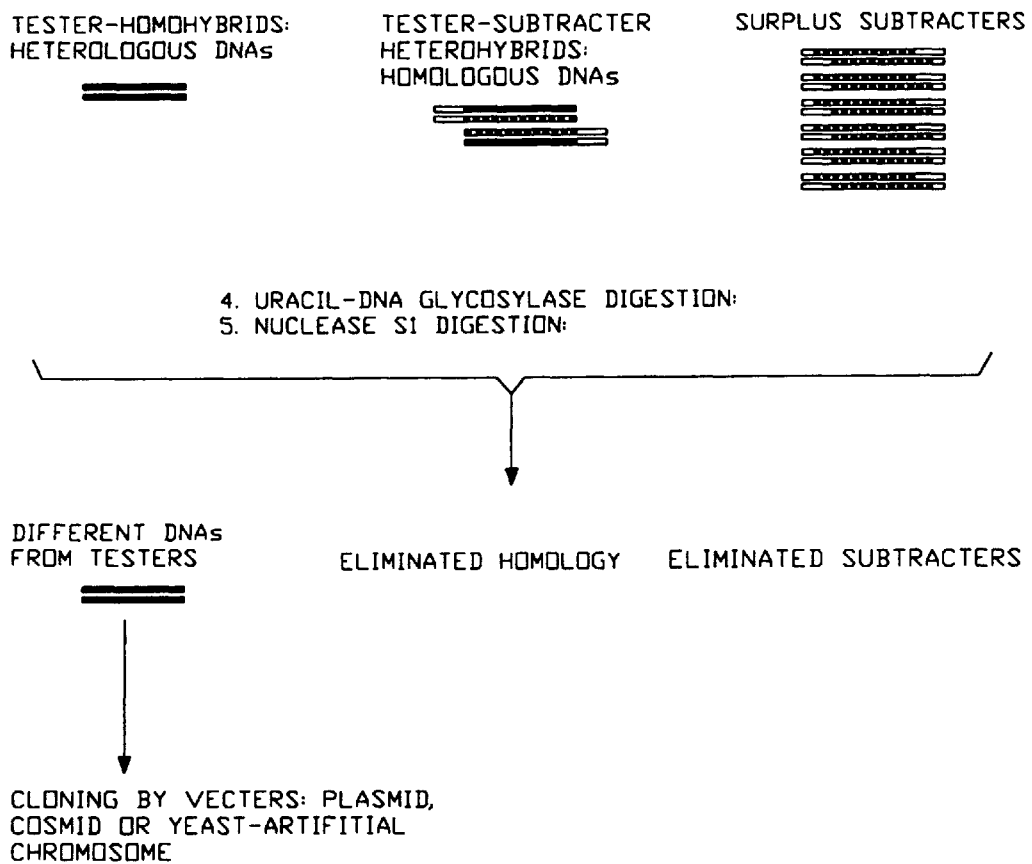
Figure 6A:
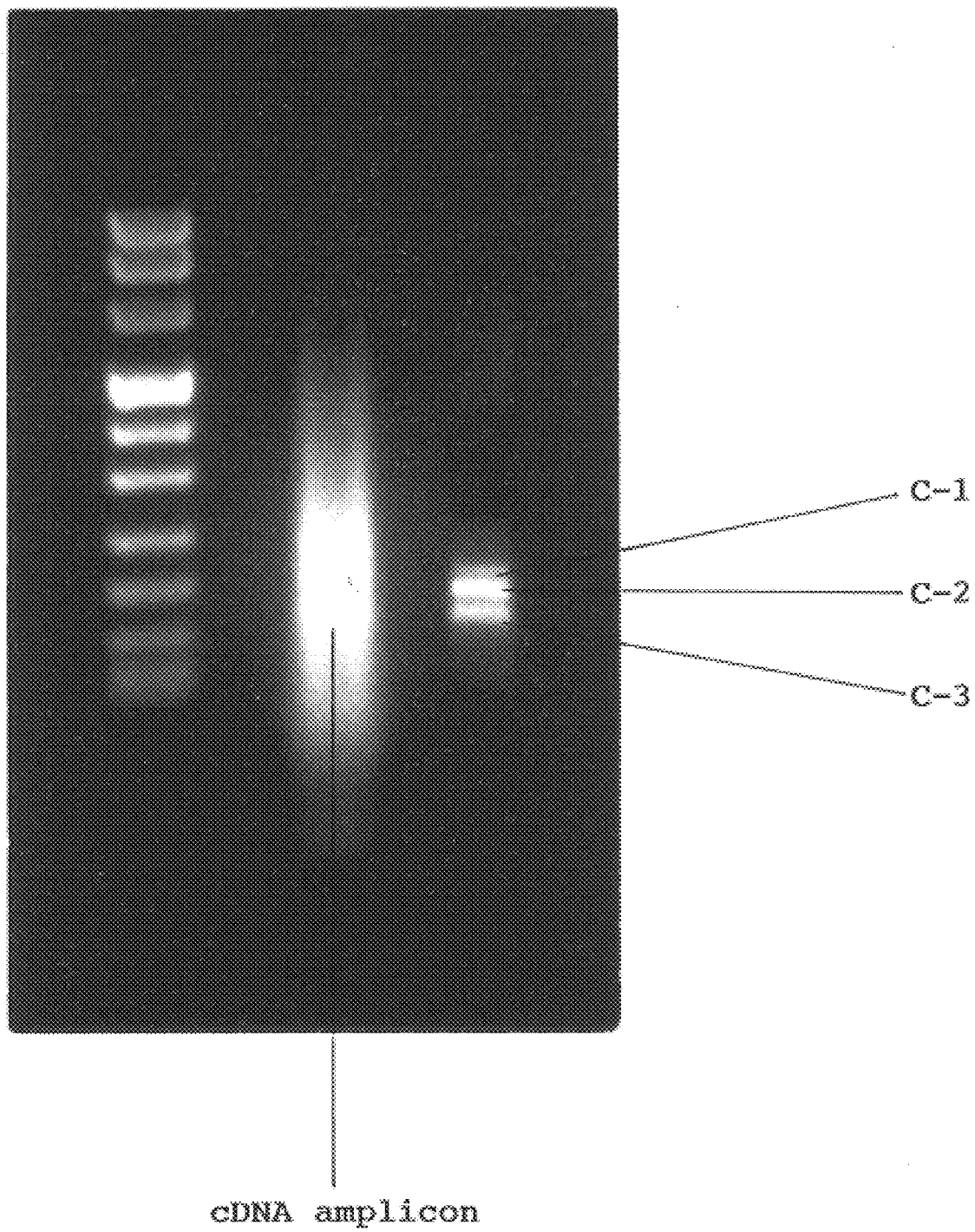
FIGS. 6A–6D are the results of examples 4, 6 and 7 of the subject invention.
Figure 6B:
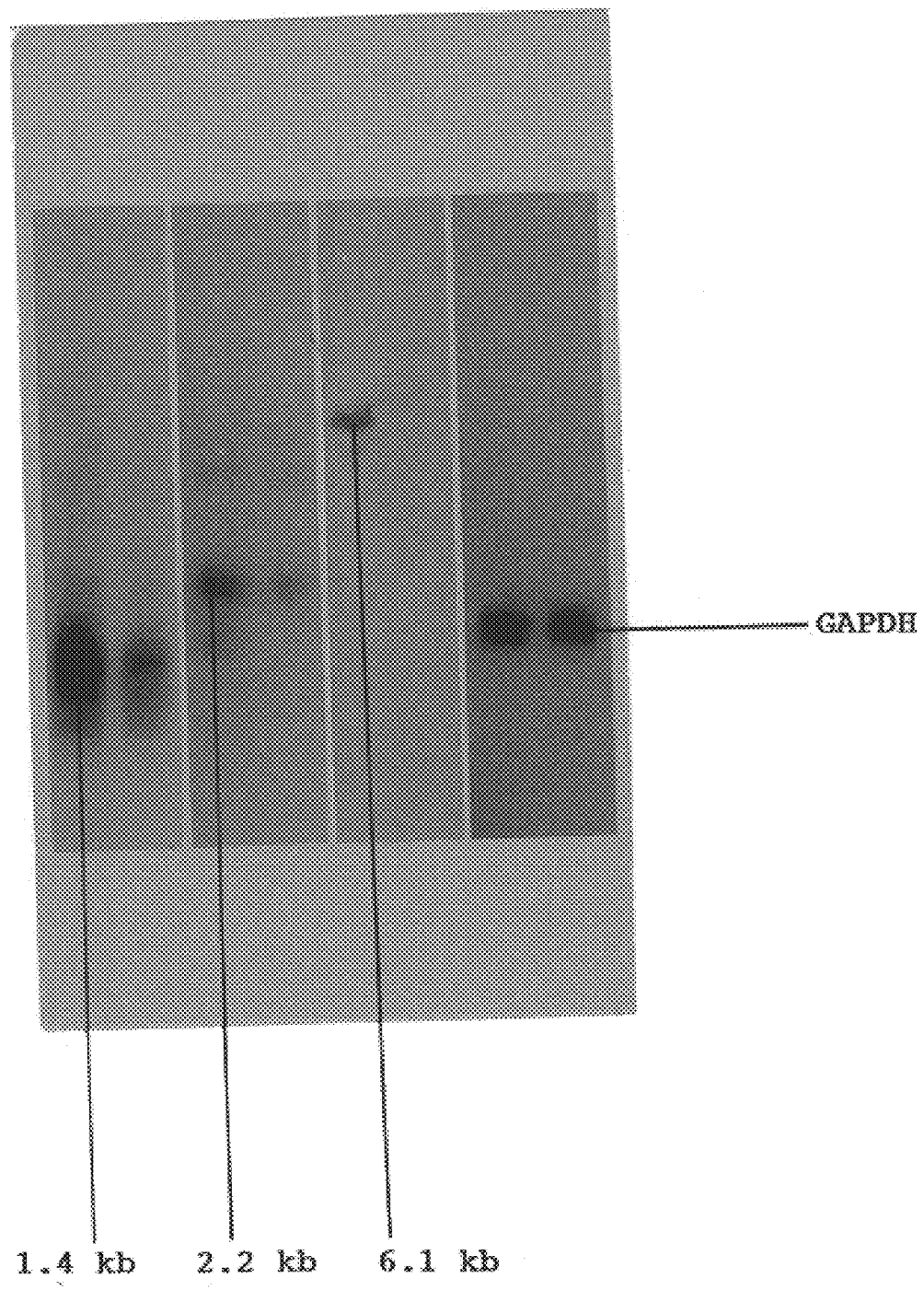
Figure 6C:
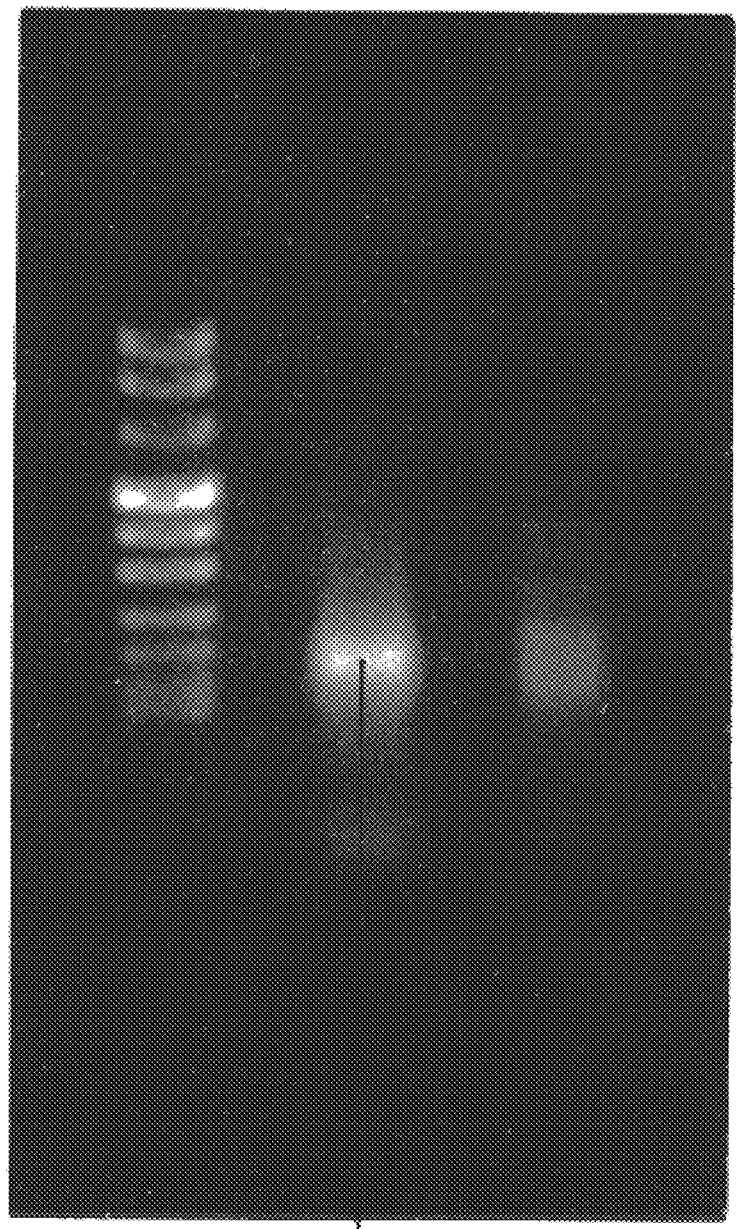
Figure 6D:
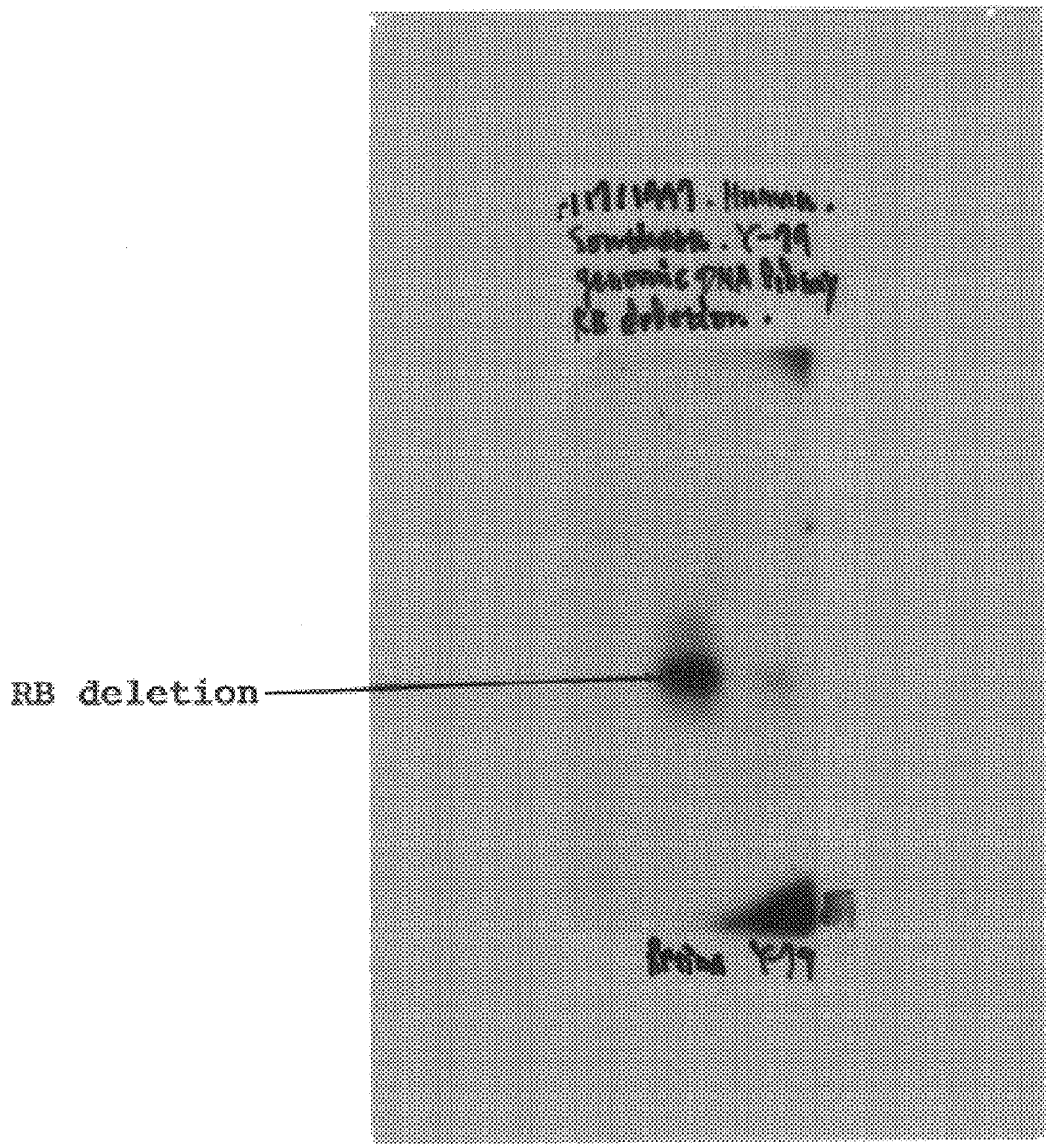

For nucleotide analog-incorporation, the control DNA was digested by a restriction-endonuclease on both ends, preferably a 4-cutter restriction enzyme, and ligated to a specific adaptor. This ligated DNA called subtracter-amplicon is then used to generate nucleotide analog-containing subtracter DNA by a template-dependent primer-extension reaction in the presence of nucleotide analog, preferably by a uracil-incorporation PCR as in the step 2 of FIG. 3 and 4. Although the specially designed adaptors/primers were used to generate subtracter DNA, any oligonucleotide capable of being extended into nucleotide analog-containing subtracter DNA for the purpose of enzymatic subtraction is within the scope of the present invention. The enzymatic subtraction refers to the elimination of common sequences by the sequentially enzymatic digestion in a subtractive hybridization assay. After nucleotide analog-incorporation, the adaptor part of a subtracter DNA can be either removed by a restriction-enzyme (if the same adaptor is used to generate tester-amplicon) or kept on both ends (if adaptors are different from each other as shown in FIG. 3). Thus, when the starting material is very limited, tester DNA will need to be amplified by a similar procedure as for the subtracter but without the nucleotide analog-incorporation. In another case (as shown in FIG. 4), when the starting material is abundant, tester DNA only needs to be digested by the same restriction-enzyme as does subtracter-amplicon but without the ligation; and after a subtractive hybridization which contains a filling-the-ends reaction before the enzymatic digestion, the blunt-ended desired sequences can escape the digestion and be amplified by a cloning procedure.

In the step 3 of FIGS. 1–5, tester DNA is then mixed with an excess amount of nucleotide analog (preferably dU)-incorporated subtracter, denatured, and hybridized at cooler temperature, preferably 60–75° C., most preferably 65–68° C. (Lehninger, et al., "*Principles of Biochemistry*, 2nd Edition", p343; Sambrook et. al., "*Molecular Cloning*, 2nd Edition", p10.45). It is preferred that the ratio of subtracter to tester DNA is in the range of about 10:1 to about 150:1. In the most preferred embodiment, the ratio is between 30:1 to 60:1. If the ratio of subtracter to tester is too high, successful enrichment of sequences that are only up- or down-regulated/changed by several fold will not be obtained. If the ratio of subtracter to tester is too low, common sequences will not be completely selected out, and then cause false-positive results which need to be removed by more rounds of subtraction. The optimal ratio of subtracter to tester DNA for isolating a particular sequence will vary depending on the amount of difference between tester and subtracter.

During the hybridization step, three kinds of hybrid duplexes are formed as follows: First, the tester-homohybrid duplexes which consist of heterologous (different) sequences only present in tester but almost absent in subtracter; Second, the tester-subtracter-heterohybrid duplexes which consist of homologous (common) sequences present in both tester and subtracter; And third, the subtracter-homohybrid duplexes which consist of surplus subtracter. Only the ones lacking any nucleotide analog-containing DNA structure will be spared from the sequential digestion of nucleotide analog-removing enzyme and single-strand-specific nuclease; therefore, the tester-homohybrid duplexes can be preserved intact throughout the sequentially enzymatic digestion, whereas the subtracter-subtracter and tester-subtracter duplexes are digested into very small fragments which can not be amplified or cloned. For example, as shown in FIGS. 3 and 4, the UDG cleaves the uracil-bases from uracil-containing hybrid DNAs, resulting in many abasic-nicks and -gaps generated within the subtracter-subtracter and subtracter-tester duplexes (step 4). The nuclease S1 then digests all nicks and gaps to make these abasic sequences into undetected and unamplifiable pieces (step 5). Although the UDG and nuclease S1 were used in a preferred version of the present invention, any enzyme or enzyme-combination capable of digesting subtracter and common sequences in the same matter is within the scope of the present invention. Such contemplated nucleotide analog-removing enzymes and single-strand-specific nucleases for use in the step 4 and 5 include uracil-N-glycosidase (UNG), AP endonuclease and Mung-Bean nuclease (MBN).

In a preferred embodiment, referring to FIG. 2, when the adaptor of subtracter is removed after nucleotide analog (preferably dU)-incorporation, the tester-homohybrid duplexes will contain adaptor on both ends, whereas the tester-subtracter-heterohybrid duplexes have 5'-adaptor on only one end (step3 in FIG. 2). This results in an exponential amplification of the tester-homohybrid duplexes and a linear amplification of the tester-subtracter-heterohybrid duplexes during an optional selective amplification (step 6 in FIGS. 1 and 2), which can be completed before or after the sequentially enzymatic digestion to emphasize the differences. In this preferred embodiment, selective amplification is accomplished after the sequentially enzymatic digestion for completely preventing any amplification of the tester-subtracter duplexes.

Alternatively as shown in FIG. 3, when the tester-adaptor is different from the subtracter-adaptor, subtractive hybridization can be performed directly without removing the subtracter-adaptor since a mismatched adaptor on both ends will form a single-stranded region (step3 in FIG. 3). In this case, the sequentially enzymatic digestion must be completed before selective amplification for cleaving the mismatched adaptor from the tester-subtracter duplexes, resulting in no amplification during selective PCR. However, since the sequentially enzymatic digestion destroys all contaminating nucleotide analog-containing duplexes, this procedure ensures that only the tester-homohybrid duplex can be isolated at final. Thus, the removing of adaptor confers additional subtraction force for reducing the potential contamination from tester-subtracter or subtracter-subtracter duplexes.

The subtracted tester DNA can be subjected to another round of subtraction or amplified by PCR. The final subtracted or selectively amplified sequences are used for DNA library selection assay and clonal analysis, and represent the desired different DNAs which are stimulated or up-regulated in the treated, mutated, infected, differentiated, or abnormal cells. By the same token, the tester and subtracter steps can be done in reverse order to isolate the suppressed or down-regulated DNAs. The final isolated sequence can then be used to probe the full-length mRNA or cDNA from the tester library (if cDNA tester is used), or to locate the deleted/inserted loci in a special chromosome by in-situ-hybridization (if genomic DNA is used). The information so obtained will provide further understanding of a variety of diseases, physiological phenomena, and genetic functions.

The present invention will be very useful in the identification of different gene expression involved in development, cell differentiation, aging, and variety of pathological disorders, such as cancer formation, genetic defects, autoimmune diseases, and any other disorders related to genetic malfunction. The identification of these differentially expressed genes will help the determination of their open-reading frames and corresponding peptides which may contribute to a specific drug-design or therapy for regulation of theses genes. Such therapeutic approaches include transcription inhibitors, monoclonal antibodies, antisense RNA, and chemicals that can interact with the gene or its protein product to cure or alleviate related disorders. For example, the methods of the present invention can be used to screen candidate genes for gene therapy to correct inherent defects. When a defect is caused by stimulation of a specific unknown gene, the identification of this gene will help the design of antisense ogilonucleotides against the gene or production of monoclonal antibodies against the corresponding protein product.

Alternatively, the present invention can also be used to screen some types of chromosomal abnormalities, such as deletion and insertion. Because genomic DNA fragments of less than one kilobase are prepared by restriction-enzyme digestion before subtractive hybridization (Lisitsyn et. al., *Science* 259: 946–951(1993)), the target deletion or insertion must be larger than this size for efficient amplification. The identification of these chromosomal deletions or insertions may contribute to the diagnosis or prognosis of certain virus infections, inherent problems, or developmental defects. For example, p16 deletion is very well known to happen in familial melanoma. If the deletion can be identified as early as possible, this information may help potential patients to prevent the onset of melanoma.

Although nucleotide analog-containing DNA subtraction assay (NDSA) is primarily designed for medical and biological research, the method will also be useful to pharmaceutical, agricultural, and environmental research which involves biological systems. For example, when the gene expression is compared between drug-treated and non-treated cells, the results may indicate the mechanism by which this drug acts. For another example, when the genomic DNAs from disease-resistant plant cells are compared with those from disease-susceptible plant cells, the results will be the candidate loci for the resistant gene(s). Taken together, the NDSA is capable of providing variety of information for understanding the changes of gene expression and the differences between genomes.

In the preferred embodiments (as shown in FIG. 3 and 4) of the present invention, according to the high activity of UDG- and nuclease S1-digestion, the labor- and time-consuming factors in this subtractive hybridization assay can be reduced to the minimum. Also, the preparation for uracil-containing subtracter DNA is cheaper and more efficient than other "modified nucleotide"—or "nucleotide analog"—incorporation which is widely used in previous methods. Most importantly, such sequentially enzymatic digestion can be carried out continuously at room temperature with the change of buffer only once. Taken together, these special features make NDSA as fast, simple, and inexpensive as a kit for concisely isolating different sequences of interest.

Although certain preferred embodiments of the present invention have been described, the spirit and scope of the invention is by no means restricted to what is described above. For example, within the general framework of (a) one or more specific adaptors/primers for nucleotide analog-incorporation and selective amplification; (b) one or more nucleotide analog-incorporation into subtracter; (c) enzyme or enzyme combination which can remove nucleotide analog or its base structure from subtracter-tester hybrid duplexes; (d) enzyme or enzyme combination which has the capability of single-strand-specific digestion for the elimination of nicked/gapped subtracter-subtracter and subtracter-tester hybrid duplexes, there is a very large number of permutations and combinations possible, all of which are within the scope of the present invention. For example, even though only UDG and nuclease S1 are shown in each of drawings, the possible substitutes could be UNG, AP endonuclease and MBN, or else that has the same functional activity.

EXAMPLE 1 cDNA Library Preparation

LNCaP cells, a prostate cancer cell line, were grown in DMEM medium supplemented with 2% fetal calf serum (FBS). For three-day activin treatment, 6 dishes of control cells were treated with 1.5 ml 200 ng/ml activin per day, while 4 dishes of experimental cells were treated with 1.5 ml 2% FBS per day. On the fifth day after the first treatment, 60% reduction in growth was observed in the activin-treated cells compared to the experimental control cells by microscopy and cell counting. The cells were trypsinized and total RNAs were isolated with TRIzol reagent (GIBCO/BRL). mRNAs were purified from total RNAs with a poly (oligo-dT) dextran column (Oligotex Direct Mini kit, Qiagen). 4 $\mu$g mRNAs were mixed with an oligo-dT primer and heated to 65° C. (10 min). Reverse transcription (RT) was performed with an oligo-dT primer following the manufacturer's protocol of cDNA Cycle kit in the Invitrogen, and the products were phenol-extracted, isopropanol-precipitated and resuspended in 40 $\mu$l 10 mM Tris-buffer. All RT products (2~3 $\mu$g) were used to synthesize second strand cDNAs (ds-cDNAs) with a DNA polymerase1-T$_4$ ligase-RNase H mixture (Ueli et. al., *Gene*, 25: pp263–269 (1983)). 500 ng of experimental double-stranded cDNAs were digested by a four-cutting enzyme, such as 5 U/$\mu$l Hpa2 (4 h, 37° C.), and prepared for 5'-end ligation in a pre-reaction volume of 47 $\mu$l containing: 1 $\mu$l 4 $\mu$g/$\mu$l T-hpa-24mer oligo, 1 $\mu$l 2 $\mu$g/$\mu$l dephosphorylated T-hpa-12mer oligo, 5 $\mu$l ligase buffer and ddH$_2$O. Before 3 $\mu$l 5 U/$\mu$l T$_4$ ligase was added, the 47 $\mu$l mixture was heated to 50° C. (2 min), and gradually cooled down to 10° C. over a period of one hour, and then the ligation was performed at 14° C. (16 h). This formed the tester-amplicon. For subtracter-amplicon generation, 500 ng Hpa2-restricted control cDNAs were ligated to the S-hpa-12/24mer adaptors in the manner described above.

Uridine analogs were incorporated into the subtracter sequence as described below.

EXAMPLE 2

Uridine Analog-incorporation

The subtracter-amplicon was diluted to 10 µg/ml, and four PCR reactions were set up on ice to generate subtracter U-DNA for the control set. Each 50 µl reaction contained 2 µl diluted ligation, 1 µl 4 µg/µl S-hpa-24mer oligo, 2 µl dNTPs (10 mM dATP, 10 mM dCTP, 10 mM dGTP, and 30 mM dUTP), 5 µl 10× PCR buffer, 1 µl 3.5 U/µl Taq DNA polymerase and ddH$_2$O. The S-hpa-12mer was melted away (5 min, 72° C.), and ends filled in with Taq DNA polymerase (7 min, 72° C.). Twenty-one cycles of amplification were performed (1 min, 95° C.; 3 min, 72° C.), and the products were phenol-extracted, isopropanol-precipitated and resuspended in 20 µl 10 mM Tris-buffer each (Sambrook et. al., "*Molecular Cloning, 2nd Edition*", p10.49 (1989)). The S-adaptors were then removed with Hpa2-restriction, and the restricted products (subtracters) were phenol-extracted, isopropanol-precipitated, combined and resuspended in a total 16 µl EEx3 buffer (30 mM EPPS, pH 8.0 at 20° C.; 3mM EDTA). 6 µl (9 µg) subtracters were measured on a 2.5% TBE-agarose gel.

The tester cDNA fragments were hybridized with subtracter U-DNA fragments as described in the following example.

EXAMPLE 3

Subtractive Hybridization and Selective Amplification

For subtractive hybridization, 300 ng of T-adaptor-ligated tester-amplicon (testers) from non-treated cells was dissolved by 10 µl subtracter-containing solution and denatured at 98° C. (6 min). The mixture was then cooled on ice (2 min), added with 2 µl 5M NaCl to adjust salt concentration, vortexed, overlaid mineral oil, and incubated at 67° C. (20 h). The hybridized-DNAs were diluted with 20 µl MgCl$_2$ solution (2.5 mM) and two 50 µl PCR reactions were set up with 2 µl diluted hybrids, 1 µl 4 µg/µl T-hpa-24mer oligo, 2 µl dNTPs (10 mM dATP, 10 mM dCTP, 10 mM dGTP, and 10 mM dTTP), 5 µl 10× PCR buffer, 1 µl Taq/Pwo DNA polymerase mixture (3.5 U/µl) and 39 µl ddH$_2$O. The T-hpa-12mer was melted away (5 min, 72° C.), and ends filled in with Taq/Pwo DNA polymerase (7 min, 72° C.). Six-cycles of amplification were performed (1 min, 95° C.; 3 min, 70° C.), and the products were phenol-extracted, isopropanol-precipitated and resuspended in 17 µl 1× PCR buffer.

Enzymatic digestion of hybridized DNA was accomplished as described below.

EXAMPLE 4

Sequentially Enzymatic Digestion

5 µl uracil-DNA glycosylase (1 U/µl) was added (2 h, 20° C.) to above products to remove uracil-bases, resulting in generating abasic-nicks/gaps in the tester-subtracter hybrids and surplus subtracters. These abasic-sites were then susceptible to the nick/gap-digestion of 1 µl 2 U/µl nuclease S1 (30 min, 25° C.), and then the digest was phenol-extracted, isopropanol-precipitated and resuspended in 20 µl 10 mM Tris-buffer. Final selective amplification were set up on ice, containing: 2 µl digest, 1 µl 4 µg/µl T-hpa-24mer oligo and same as aforesaid. The procedure was as described above, with the differences that 1 µl Taq/Pwo DNA polymerase mixture was added at 80° C. and a twenty-cycle PCR was performed. Final products were combined, phenol-extracted, isopropanol-precipitated and resuspended with 20 µl 10 mM Tris-buffer to give the desired different sequences. Recovery of the final product was accomplished by Gel Extraction (Qiagen kit) from electrophoresis on 2.5% agarose gel (FIG. 6-A).

The subtracted library was constructed as described below.

EXAMPLE 5

Cloning and Sequencing of Difference Products

Final difference products were cloned into the blunt site of a pCD21 vector using a Clontech TA Cloning kit. The double-stranded vector was amplified in INVαF' cells (Invitrogen), prepared using a miniprep column (Qiagen), and sequenced with Sequenase v.2 DNA sequencing kit (Amersham) by dideoxy-mediated chain termination. Resulting sequences were searched and compared to the Genbank database using the BLAST program.

The successful isolation of differentially expressed genes was confirmed by Northern blot hybridization as described below.

EXAMPLE 6

Northern Blot Hybridization

Total RNA (8 µg) isolated from both non-treated and activin-treated LNCap cells was separated by electrophoresis through 0.9% agarose-formaldehyde gel and transferred to nylon filter (Schleicher & Schuell). The filter was dried and baked under UV-light (30 sec.) DNA probes from three PCR-amplified inserts (probe C-1, C-2, and C-3 in FIG. 6-A) were prepared with a Prime-It random labeling kit (Strategene) in the presence α-[$^{32}$P] dATP. Northern blot hybridization was carried out for 4 hours at 68° C. in QuikHyb solution (Strategene). Blots were washed with 2% SSC, 0.1% SDS solution at room temperature twice (15 min each), followed by a 1 hour wash in 0.1% SSC, 0.1% SDS solution at 65° C.

As shown in FIG. 6-B, three specific mRNAs of approximately 1.4, 2.2 and 6.1 kilobase were detected in the non-treated cells but much less in the activin-treated cells by C-2, C-3, and C-1, respectively. The sequencing result of the 6.1 kilobase mRNA confirmed a down-regulation of Bcl-2 gene expression which is highly related to growth reduction of activin-treated LNCaP cells.

EXAMPLE 7

Detection of Genomic Deletion in Retinoblastoma Cells

Y-79, a retinoblastoma cell, has been known to contain an RB-deletion in its genome. As a model of genomic subtraction by USA, the genomic DNAs of normal retina cells and Y-79 cells were isolated by the IsoQuick nucleic acid extraction kit (Microprobe), restricted with Hpa2, and ligated to T-hpa-adaptor and S-hpa-adaptor respectively to give the tester (normal cell) and subtracter (Y-79). The size of restricted genomic DNA was about 1 kilobase which can be efficiently amplified by PCR. The uridine analog was incorporated into subtracter as described in Example 2. The subtractive hybridization method described in Example 3. was accomplished following by sequentially enzymatic digestion described in Example 4. The resulting subtracted tester DNA (FIG. 6-C) was amplified by PCR, cloned into a prokaryotic expression vector, and used to transform competent cells. These cloned DNA fragments were then purified, random-prime labeled, and used to probe a Southern blot of genomic DNA fragments isolated from tester and subtracter. A signal was detected on the normal DNA but not Y-79 DNA (FIG. 6-D). The sequencing result of this signal indicated a 108 base deletion in RB-exon 1.

Alternatively, the present invention is directed to an improved subtractive hybridization method, called covalent homologue subtraction (CHS) assay, for screening desired different sequences between two cDNA or genomic DNA libraries. This method is primarily designed for quickly isolating different expression genes (either up- or down-regulated), easily detecting large genomic deletions/insertions, and precisely searching chromosome-specific loci. The principle of CHS is dependent on the subtraction force of covalent-bonding between homologues sequences (homologues) during a PCR or cloning, resulting in no amplification of the homology. The preferred version of the present invention is based on: the single-stranding modification of subtracter DNA, the covalent modification of the subtracter's base structures, the hybridization of the modified subtracter and non-modified tester DNA to covalently subtract common sequences, and a tester-specific amplification to amplify the signal of desired different sequences. In conjunction with an adaptor-ligation and a specific PCR amplification, a very small amount of DNA library can be used as an initial sample for this method.

As used herein, tester DNA refers to the DNA isolated from a treated, mutated, infected, differentiated or abnormal cell source, while subtracter DNA refers to the DNA isolated from a cell source with different status, such as non-treated, un-/further-differentiated, or relatively normal cells (or tissues containing homogeneous cells). And, such referring can be done vice versa. The tester DNA library contains desired sequences which are abundant in the tester but very limited in the subtracter. The desired sequences represent the differences of gene expression (if a cDNA library is used as sample), or those of genomic complexity (if a genomic DNA library is used). The isolation of the desired sequences is achieved herein by using a covalence-modified subtracter DNA to remove common (homologous) sequences through hybridization and covalent-bonding, which refers to a strong heat-stable binding between the modified subtracter and non-modified tester DNA homology. The covalence-modified subtracter DNA refers to the subtracter which is purposely changed for covalently bonding with tester DNA after a covalent modification. The covalent modification refers to a reaction by which the capability of covalent-bonding with tester is render to the subtracter and is generated herein by using an amino-blocking agent and a carboxylating agent. The amino-blocking agent refers to a chemical which can block or remove the amino-group of purine bases, such as acetic anhydride and alkaline acetic chloride. And, the carboxylating agent refers to a chemical that can generate carboxyl-group on the base structure of subtracter's nucleotides in order to form covalent bonding with tester DNA, such as sodium cyanide/sulfuric acid mixture or hot alkaline potassium permanganate. The common sequence refers to the sequence which is common to both tester and subtracter DNA populations.

The advantages of using covalent homology subtracter DNA are as follows: First, during subtractive hybridization, the affinity of subtracter to homologous tester can be greatly enhanced by the covalent modification, such as the carboxyl-group on the $C_4$ of uracil/thymine or $C_5/C_6$ of pyrimidines, resulting in peptide-bonding to the tester's amino-group on the $C_6$ of adenine or $C_6/C_2$ of purines respectively (FIG. 10). Such covalent peptide-bonding between subtracter and tester fully accomplishes the completion of homologue subtraction and therefore reduces the needed amount of subtracter. Second, the covalence-modified subtracter DNA is single-stranded, resulting in high binding efficiency of tester-subtracter DNA association but very low in subtracter DNA reassociation. Third, because the covalent bonding is an internal affinity either between adenine-thymine (-uracil) or between guanine-cytosine, this covalent pairing feature significantly increases the specificity of homologue subtraction and the sensitivity of heterologous sequence detection.

For generation of tester DNA, the DNA library of experimental cells is digested by a restriction-endonuclease on both ends, preferably a four-cutter restriction enzyme, and ligated to a specific 5'-adaptor. This ligated DNA called tester-amplicon is then used to generate tester DNA by a template-dependent primer-extension reaction in the presence of a tester-specific primer, preferably using the adaptors/primers listed in FIG. 12. Although the specially designed adaptors/primers were used to generate tester DNA, any oligonucleotide capable of being extended into tester DNA for the purpose of covalent homologue subtraction is within the scope of the present invention. The covalent homologue subtraction refers to the method of common sequence elimination by forming directly covalent bonding between subtracter and tester DNA during a subtractive hybridization. On the other hand, when the starting material is very limited, subtracter DNA will also need to be amplified by a similar procedure as for the tester but with a subtracter-specific adaptor/primer which has no affinity to the tester-specific one. However, when the starting material is abundant, subtracter DNA only needs to be digested by the same restriction-enzyme as does tester-amplicon but without the ligation.

Figure 8A:
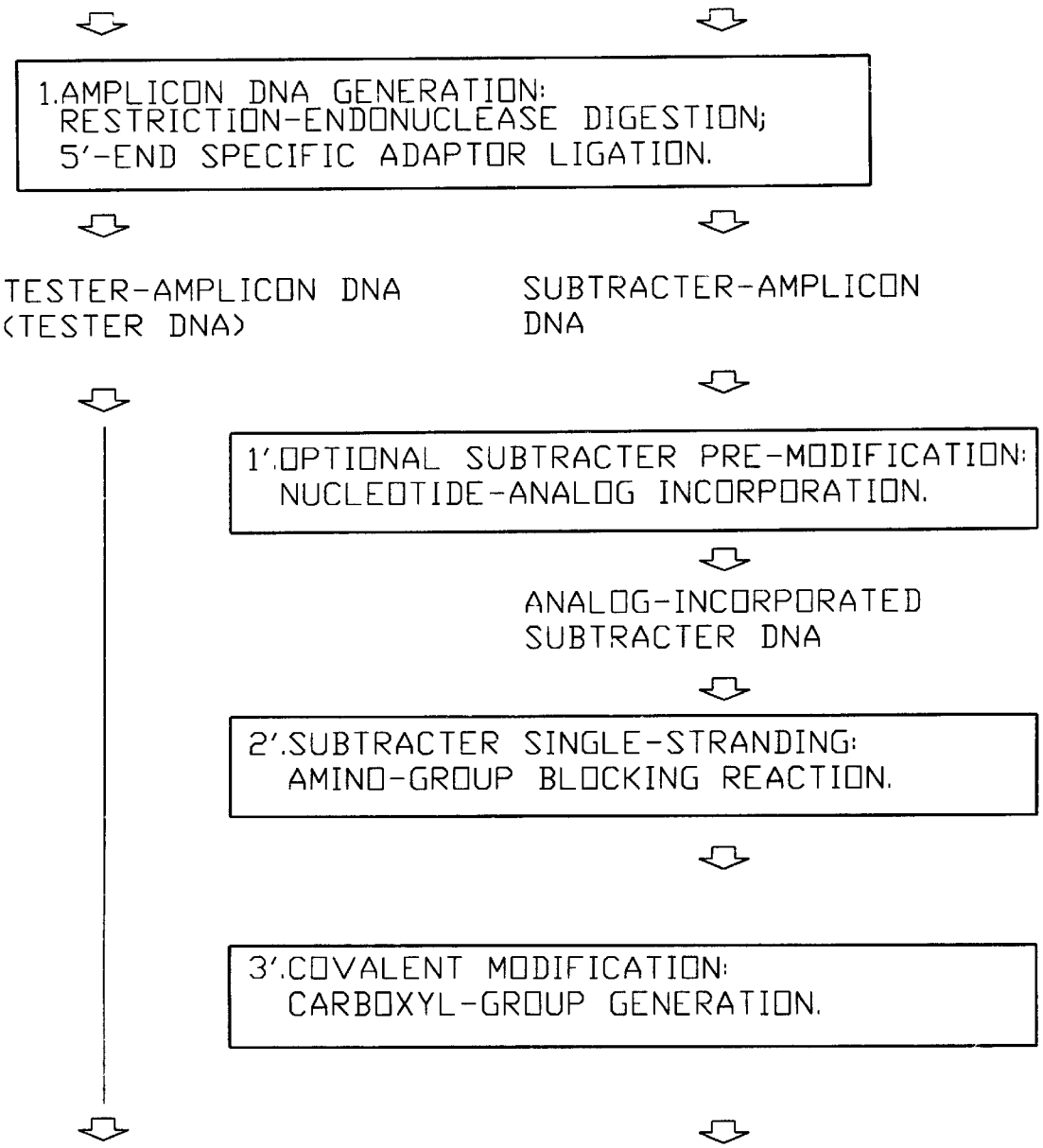
Figure 9A:
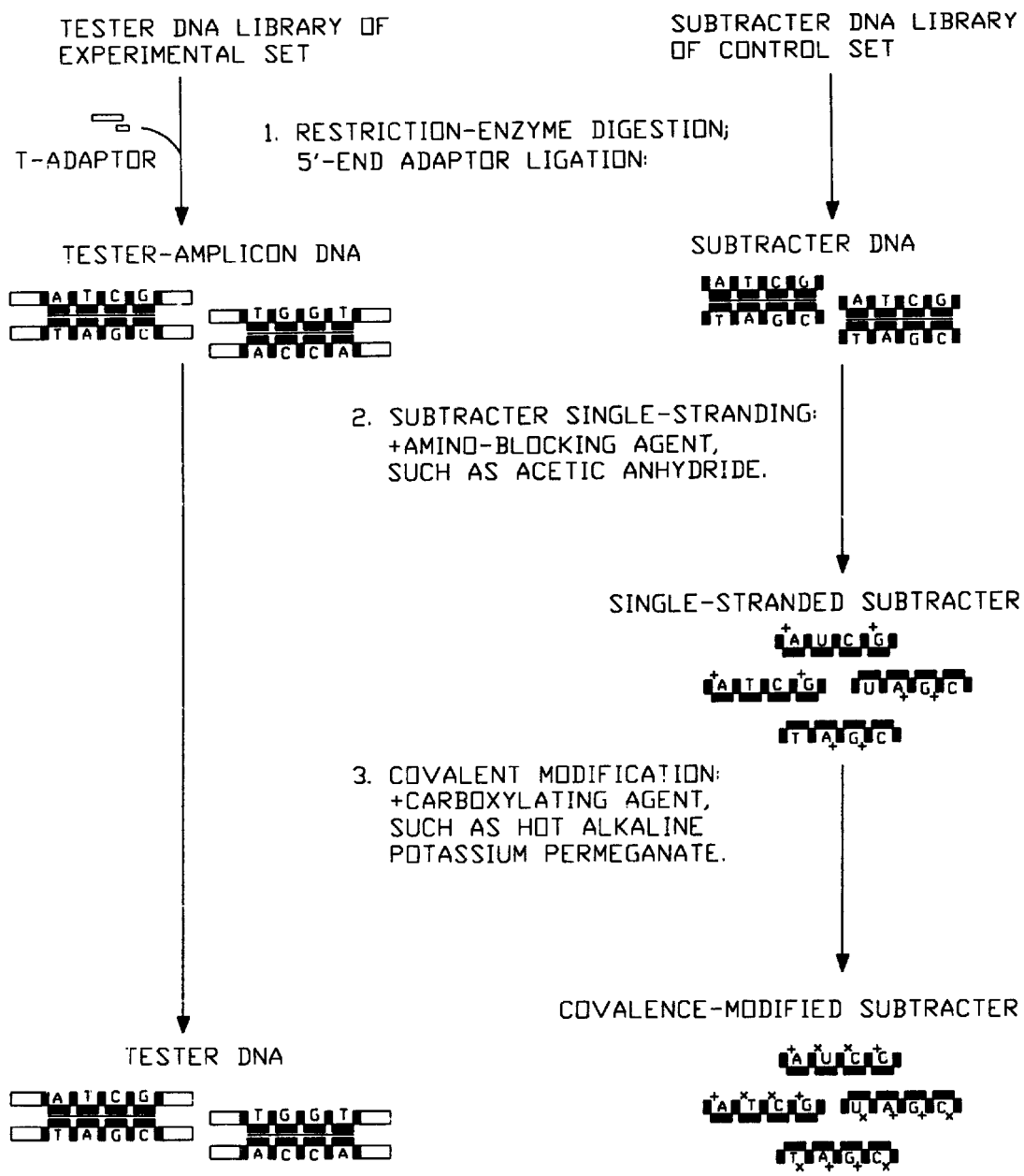
FIGS. 9a–9b is an illustration of the covalent homologue subtraction hybridization of FIGS. 8a–8b.
Figure 9B:
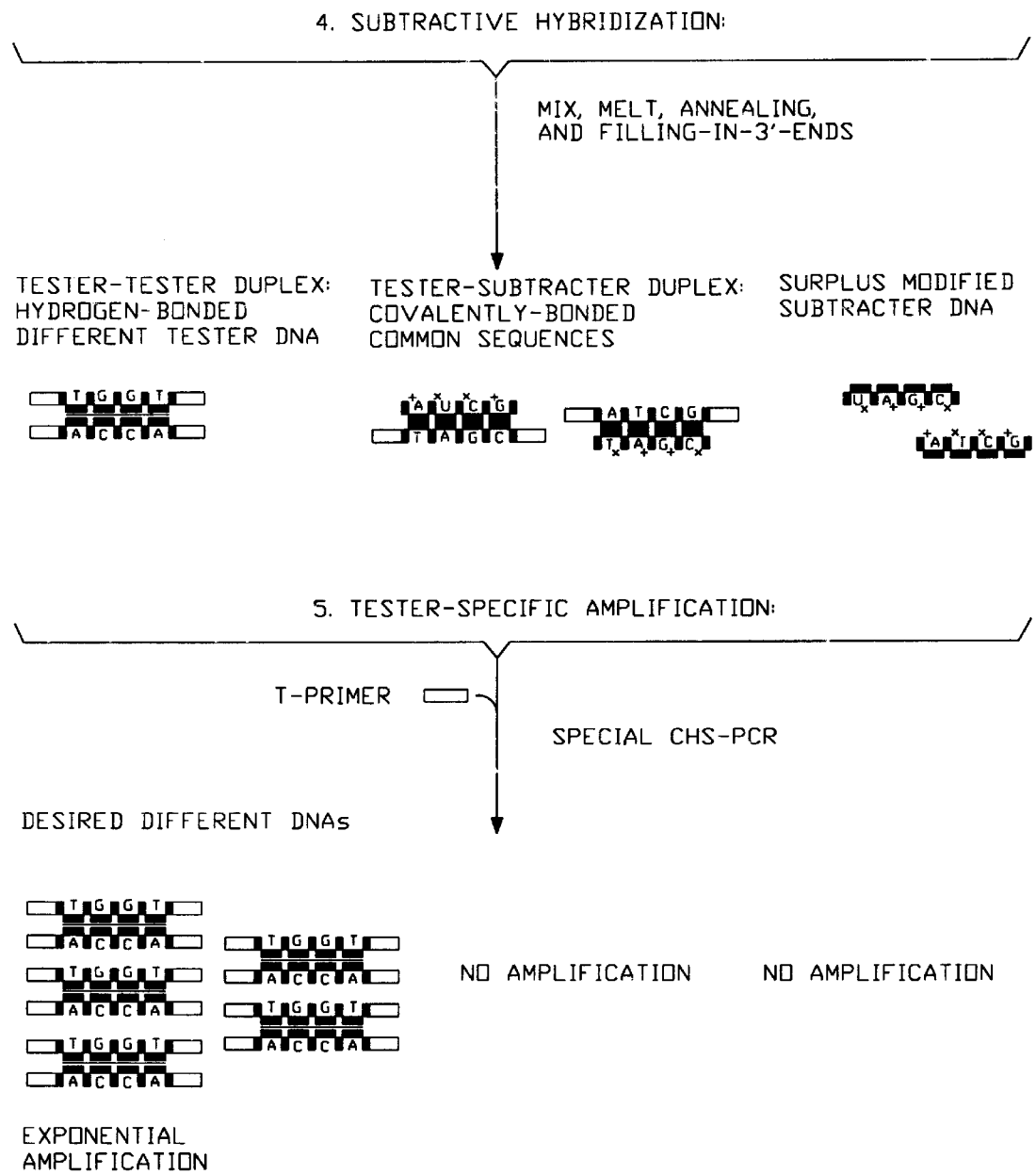
Figure 10A:
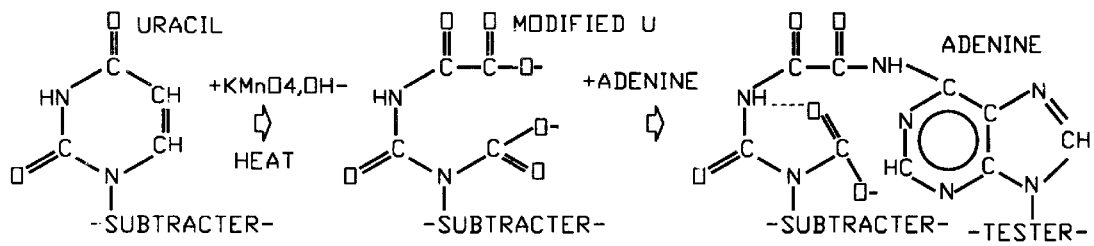
Figure 10B:
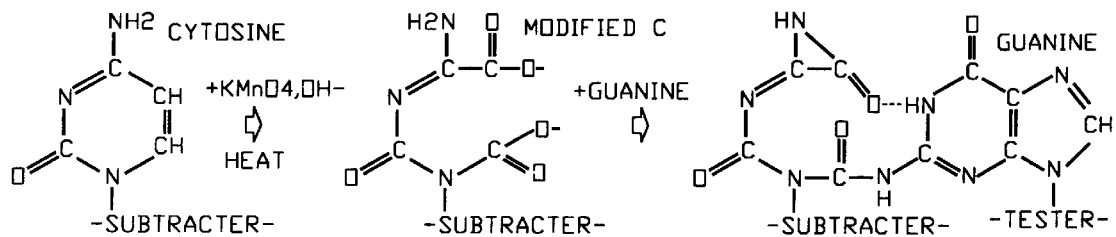
Figure 10C:
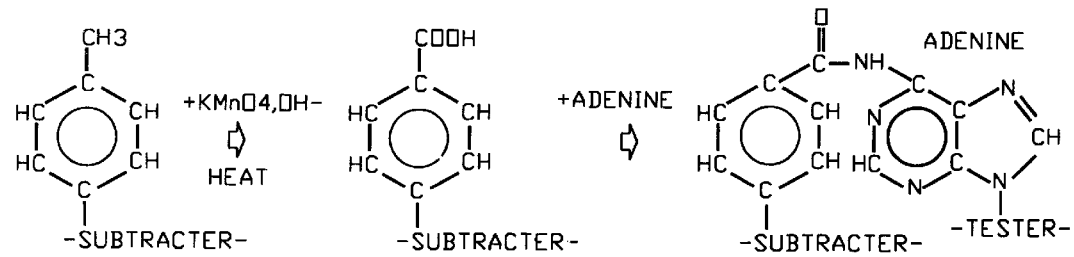
Figure 10D:
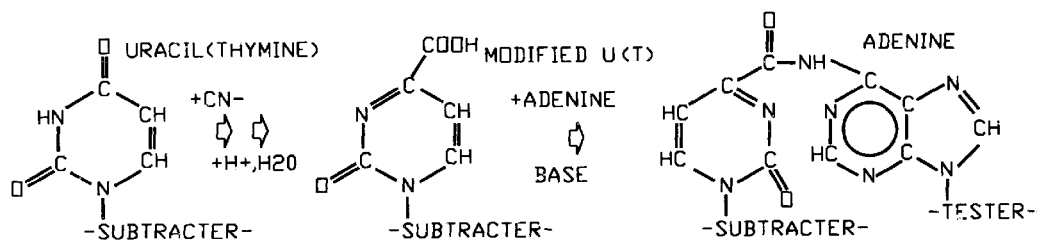
Figure 10E:
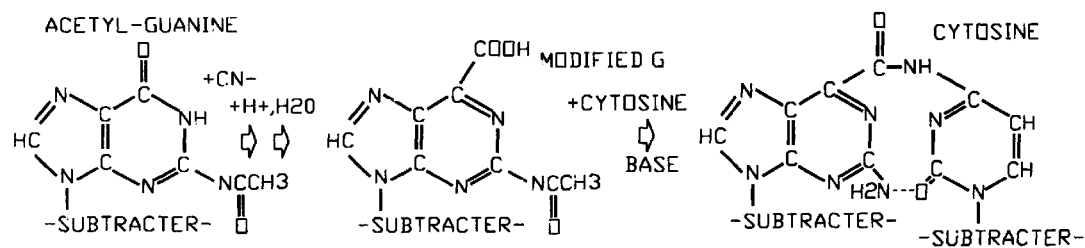
Figure 11A:
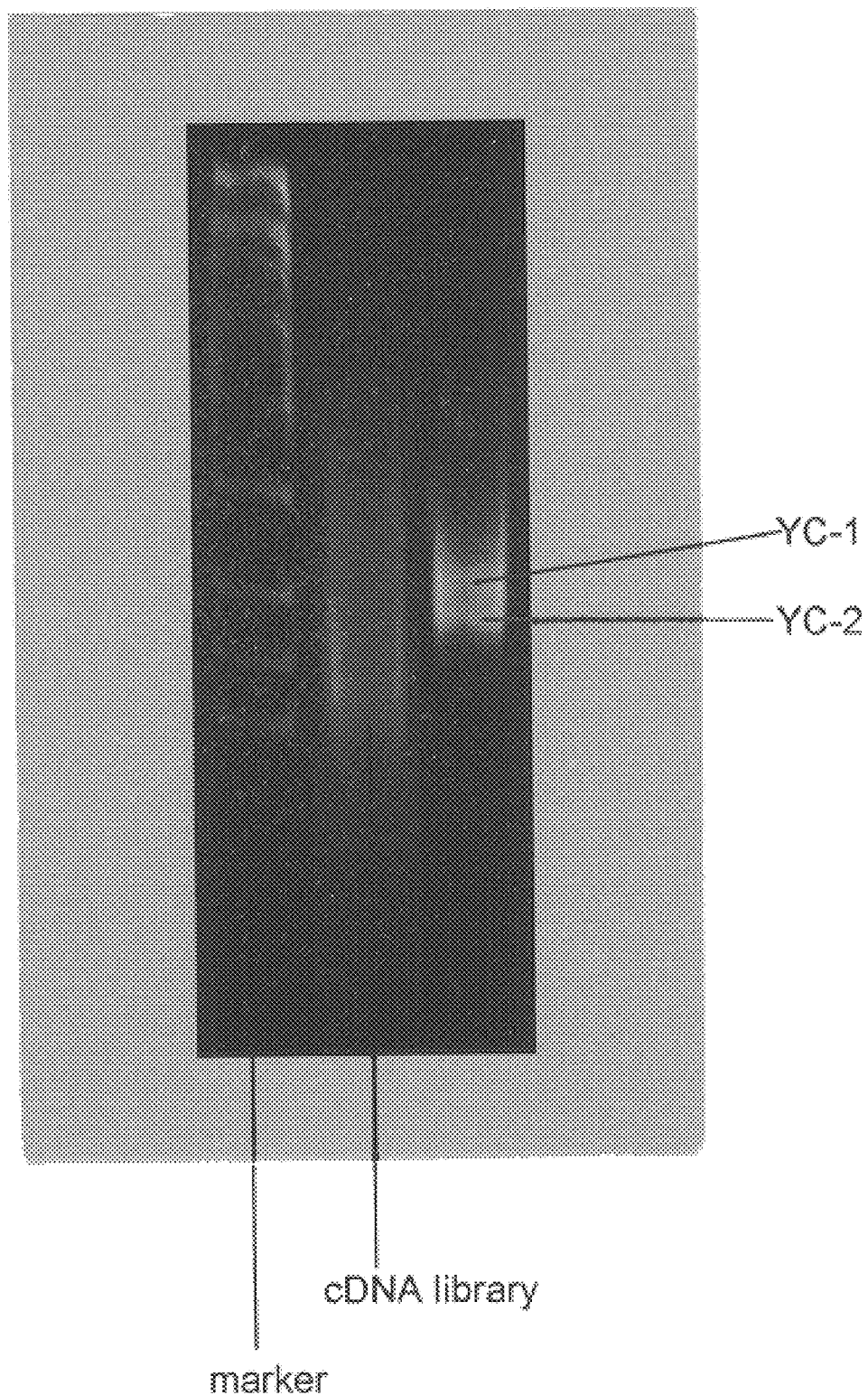
FIGS. 11A–11D are the results of examples 10, 12 and 13 of the subject invention.
Figure 11B:
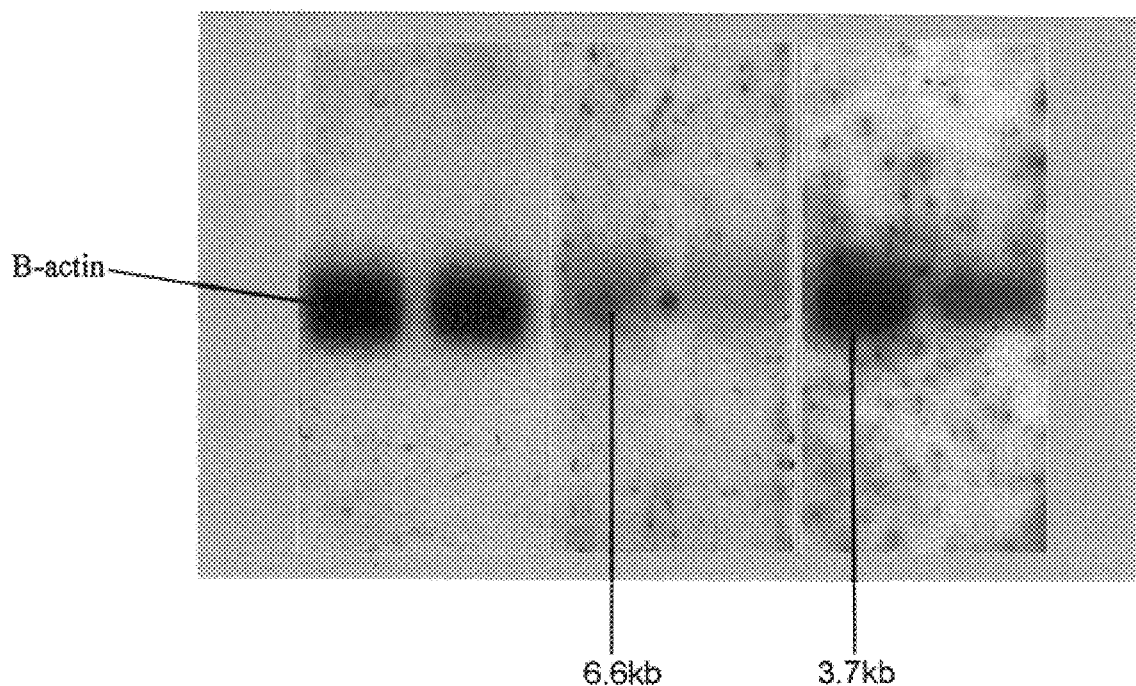
Figure 11C:
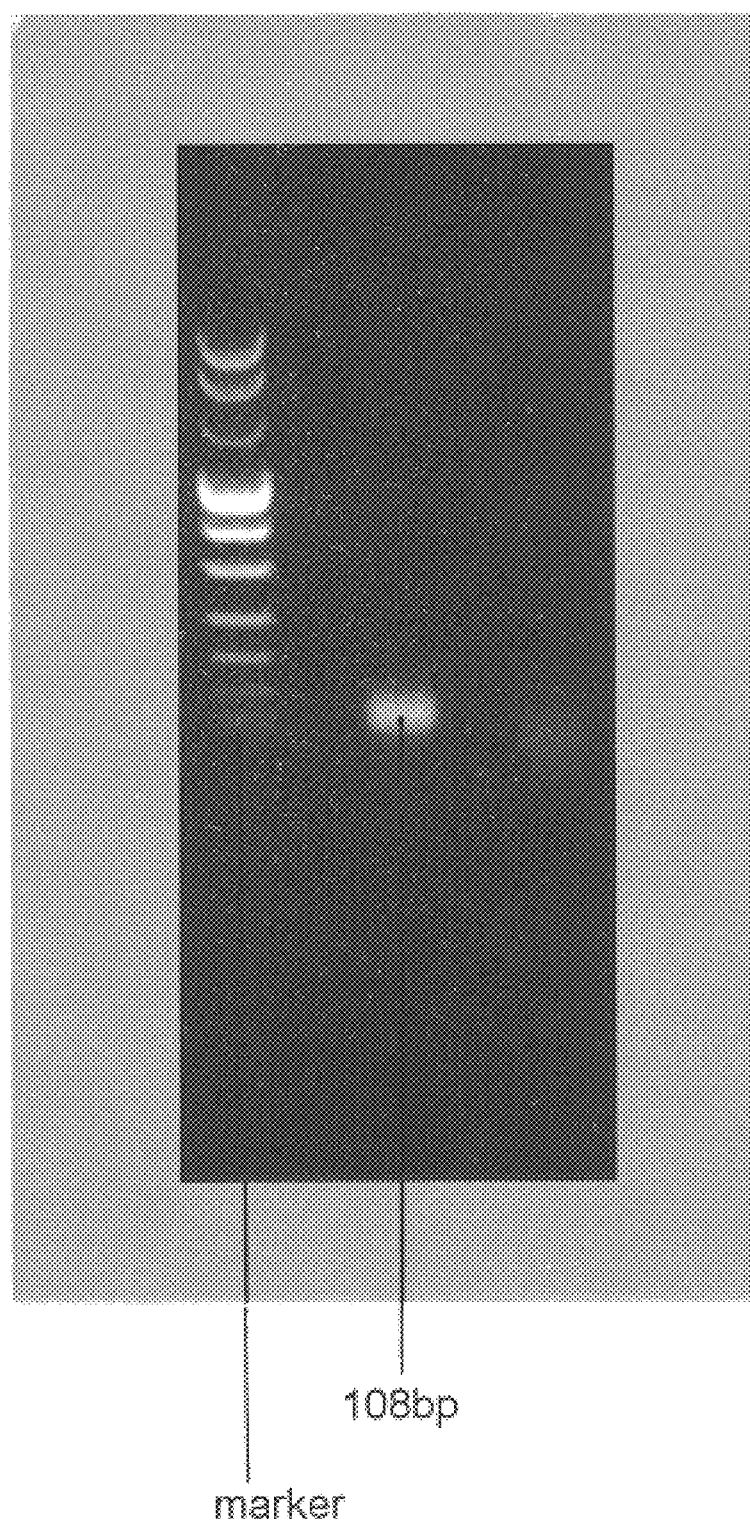
Figure 11D:
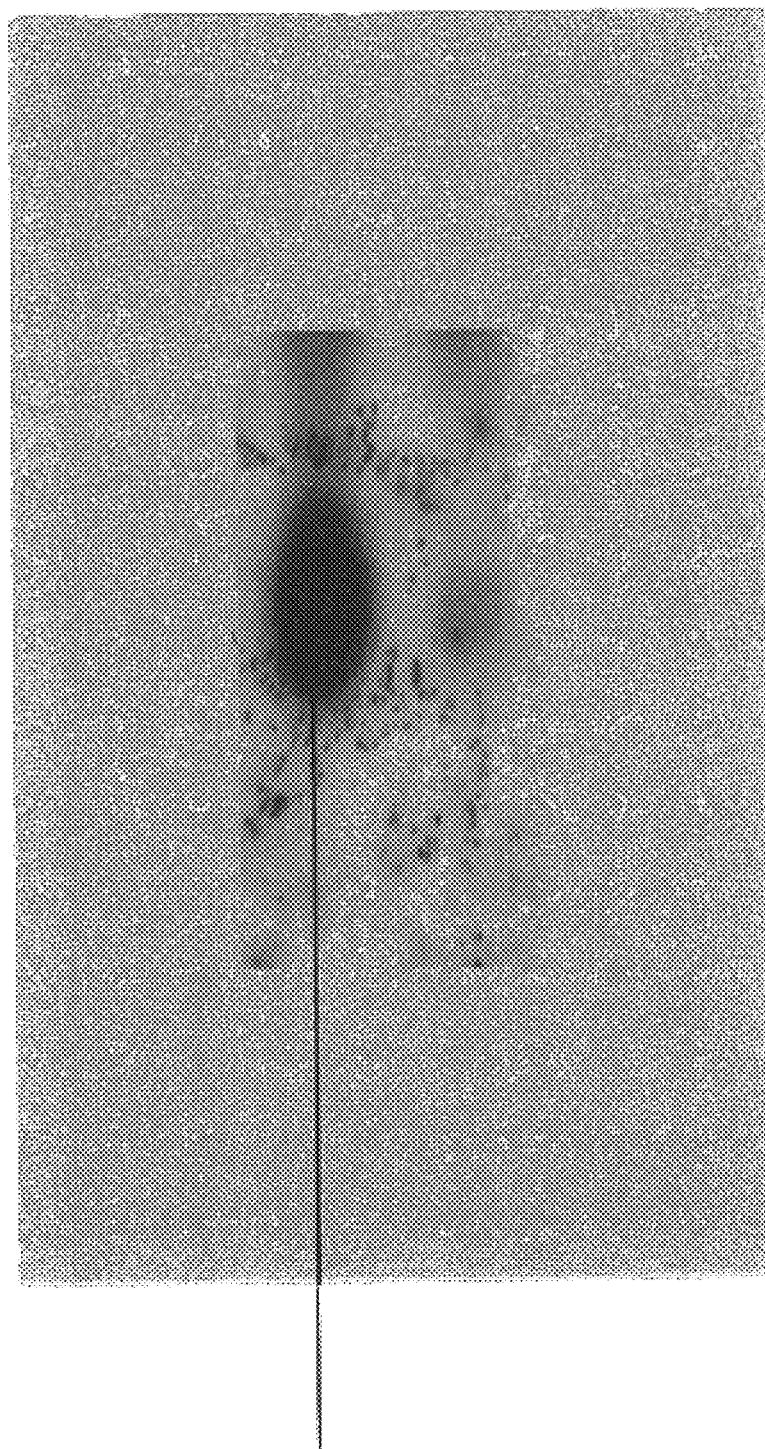

As in the step 2 of FIGS. 8 and 9, blocking activating amino-groups of subtracter must be completed before covalent modification in order to prevent the formation of covalent affinity between subtracter and subtracter sequences. This blocking reaction is preferably carried out by acetylating the amino-group of purines to form an inactive acetamido-group (Solomons et. al., 1996) which is incapable of bonding to a modified subtracter DNA, resulting in the generation of single-stranded subtracter sequences. Acetic anhydride and alkaline acetic chloride are two of preferred amino-blocking agents in the present invention. Since the single-stranded subtracter DNA can not protect the base structures of its nucleotides from oxidative agents any more, a carboxylating agent (as shown in the step 3 of FIGS. 8 and 9) then easily oxidizes the alkene, carbonyl or sometimes methyl group (Solomons et. al., 1996) of the bases into a carboxyl-group which forms a covalent peptide-bond with the non-modified amino-group of a tester DNA (FIG. 10). Hot alkaline potassium permanganate and sodium cyanide/sulfuric acid mixture are two of preferred carboxylating agents based on the principles of syn hydroxylation and nucleophilic addition respectively. Although the adenine (A), guanine (G), cytosine (C), thymine (T) and uracil (U) were used in the generation of subtracter DNA, any nucleotide or its analog capable of being incorporated and modified into subtracter DNA for the purpose of covalent homologue subtraction is within the scope of the present invention. For example, such possible substitutes could be 2'-deoxy-uracil, para-toluene like molecules, cyclohexanone like molecules or else that has the same capability of being covalently modified.

In the step 4 of FIGS. 8 and 9, tester DNA is then mixed with an excess amount of covalence-modified subtracter, denatured, and hybridized at cooler temperature, preferably 60–80° C., most preferably 68–72° C. It is preferred that the ratio of subtractor to tester DNA is in the range of about 1:1 to about 100:1. In the most preferred embodiment, the ratio is between 5:1 to 10:1. If the ratio of subtracter to tester is too high, successful enrichment of sequences that are only up- or down-regulated/changed by several fold will not be obtained. If the ratio of subtracter to tester is too low, common sequences will not be completely selected out, and then cause false-positive results which need to be removed by more rounds of subtraction. The optimal ratio of subtracter to tester DNA for isolating a particular sequence will vary depending on the amount of expression differences between tester and subtracter.

During the subtractive hybridization step, two kinds of hybrid duplexes are formed as follows: First, the tester-tester homohybrid duplexes which consist of desired heterologous (different) sequences only present in tester but almost absent in subtracter; And, the tester-subtracter heterohybrid duplexes which consist of homologous (common) sequences present in both tester and subtracter. Because the carboxyl-groups of a modified subtracter covalently bond with the amino-groups of a tester DNA, the tester-subtracter heterohybrid duplexes can not be amplified by a PCR or vector cloning in that each round of the amplification requires the separation of DNA duplexes. However, the tester-tester homohybrid duplexes are formed by hydrogen-bonds (H-bond) which can be separated during a PCR or vector cloning in order to complete their own amplification; therefore, the amount of the desired different sequences are greatly multified after a PCR or vector cloning, whereas that of common sequences will become negligible.

When the amplification of desired tester-tester duplexes is performed after covalent homologue subtraction, a tester-specific primer is needed for preventing the contamination of subtracter. Preferably, the specific adaptors/primers for tester and subtracter are those shown in FIG. 12. Additionally, such contamination can be minimized by incorporating nucleotide-analogs into the subtracter sequences during the generation of a subtracter DNA library in which the incorporated analogs are removed after hybridization and then destroyed by heat during PCR amplification. Preferably, the incorporated analogs are uridine-analogs; most preferably, the deoxy-uridine triphosphates which can be removed by uracil-DNA glycosylase. Also, the incorporated nucleotide-analogs may serve as a specific target for covalent modification, resulting in higher specificity of covalent homologue subtraction. For example, when 2'-deoxy-deoxyuridine triphosphates instead of deoxythymidine triphosphates is used to generate the subtracter library, the carboxylation reaction will only occur on the $C_4$ of uracil rather than the $C_2$ which is sometimes carboxylated if using deoxythymidine triphosphates. Preferably, here listed below are some example compounds of the incorporated analog formula:

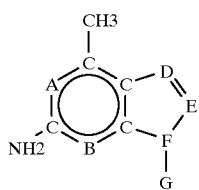

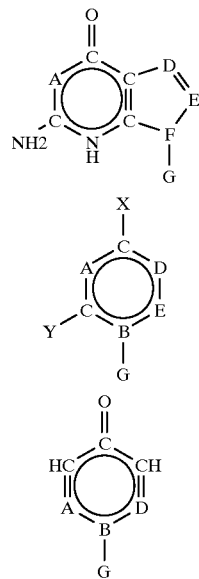

wherein A, B, D, E and F are selected from either a N or a CH group, G is a 2'-deoxy-D-ribose triphosphates, and X is a methyl group while Y is a H group and vice versa.

The subtracted tester DNA can be subjected to another round of subtractive hybridization or amplification. The final subtracted or selectively amplified sequences are used for DNA library selection assay and cloning analysis, and represent the desired different DNA sequences which are stimulated or up-regulated in the treated, mutated, infected, differentiated, or abnormal cells. By the same token, the tester and subtracter steps can be performed in a reverse order to isolate the suppressed or down-regulated sequences. The final isolated sequences can then be used to probe the full-length mRNA or cDNA from the tester library (if cDNA tester is used as a sample), or to locate the deleted/inserted loci in a special chromosome by in-situ-hybridization (if genomic DNA is used). The information so obtained will provide further understanding of a variety of diseases, physiological phenomena, and genetic functions.

The present invention will be very useful in the identification of different gene expression involved in development, cell differentiation, aging, and variety of pathological disorders, such as cancer formation, genetic defects, autoimmune diseases, and any other disorders related to genetic malfunction. The identification of these differentially expressed genes will help the determination of their open-reading frames and corresponding peptides which may contribute to a specific drug-design or therapy for regulation of theses genes. Such therapeutic approaches include transcription inhibitors, monoclonal antibodies, antisense RNA, and chemicals that can interact with the gene or its protein product to cure or alleviate related disorders. For example, the methods of the present invention can be used to screen candidate genes for gene therapy to correct inherent defects. When a defect is caused by stimulation of a specific unknown gene, the identification of this gene will help the design of antisense nucleotides against the gene or production of monoclonal antibodies against the corresponding protein product.

Alternatively, the present invention can also be used to screen some types of chromosomal abnormalities, such as deletion and insertion. Because genomic DNA fragments of less than one kilobase are prepared by restriction-enzyme digestion before subtractive hybridization (Lisitsyn et. al., *Science* 259: 946–951 (1993)), the target deletion or insertion must be larger than this size for efficient amplification. The identification of these chromosomal deletions or insertions may contribute to the diagnosis or prognosis of certain virus infections, inherent problems, or developmental defects. For example, RB deletion is very well known to happen in hereditary retinoblastoma. If the deletion can be identified as early as possible, this information may help potential patients to prevent the onset of retinoblastoma.

Although covalent homologue subtraction (CHS) assay is primarily designed for medical and biological research, the method will also be useful to pharmaceutical, agricultural, and environmental research which involves biological systems. For example, when the gene expression is compared between drug-treated and non-treated cells, the results may indicate the mechanism by which this drug acts. For another example, when the genomic DNAs from disease-resistant plant cells are compared with those from disease-susceptible plant cells, the results will be the candidate loci for the resistant gene(s). Taken together, the CHS is capable of providing variety of information for understanding the changes of gene expression and the differences between genomes.

In the preferred embodiments (as shown in FIGS. 8 and 9) of the present invention, according to the high reaction rate of covalent modifications, the labor- and time-consuming factors in this subtractive hybridization assay can be reduced to the minimum. Also, the preparation of a covalence-modified subtracter DNA is cheaper and more efficient than that of other modified subtracters in previous methods. Most importantly, such covalent modification can be carried out continuously in microtubes with only few changes of buffers. Taken together, these special features make CHS as fast, simple, and inexpensive as a kit for concisely isolating different sequences of interest.

Although certain preferred embodiments of the present invention have been described, the spirit and scope of the invention is by no means restricted to what is described above. For example, within the general framework of (a) one or more specific adaptors/primers for nucleotide analog-containing subtracter generation and tester-specific amplification; (b) one or more nucleotide analog-incorporation into subtracter DNA; (c) one or more chemical combinations which can generate covalence-modified subtracter DNA; (d) one or more rounds of hybridization and amplification to distinguish desired different sequences, there is a very large number of permutations and combinations possible, all of which are within the scope of the present invention. For example, even though only A, G, C and T/U are shown in each of drawings, the possible substitutes could be those shown aforementioned, or else that has the same functional purpose.

In one aspect, the preparation of tester- and subtracter-cDNA fragments by digestion with restriction-endonuclease and PCR amplification after ligation with an adaptor/primer is described in Example 8 below. In another aspect, the preparation of tester- and subtracter-genomic DNA fragments by digestion with restriction-endonuclease and PCR amplification after ligation with an adaptor/primer is described in Example 13 below.

EXAMPLE 8 cDNA Library Preparation

Y-79 cells, a retinoblastoma cell line, were grown in DMEM medium supplemented with 2% fetal calf serum (FBS). For three-day activin treatment, 6 dishes of control cells were treated with 1.5 ml 200 ng/ml activin per day, while 4 dishes of experimental cells were treated with 1.5 ml 2% FBS per day. On the fifth day after the first treatment, 30% reduction in growth was observed in the activin-treated cells compared to the experimental cells by microscopy and cell counting. The cells were trypsinized and total RNAs were isolated with TRIzol reagent (GIBCO/BRL). mRNAs were purified from total RNAs with a poly (oligo-dT) dextran column (Oligotex Direct Mini kit, Qiagen). 4 µg mRNAs were mixed with an oligo-dT primer and heated to 65° C. (10 min). Reverse transcription (RT) was performed with an oligo-dT primer following the manufacturer's protocol of cDNA Cycle kit in the Invitrogen, and the products were phenol-extracted, isopropanol-precipitated and resuspended in 40 µl 10 mM Tris-buffer. All RT products (2~3 µg) were used to synthesize second strand cDNAs (ds-cDNAs) with a DNA polymerase1-$T_4$ ligase-RNase H mixture (Ueli et. al., *Gene*, 25: pp263–269 (1983)). 500 ng of experimental double-stranded cDNAs were digested by a four-cutting enzyme, such as 5 U/µl Hpa2 (4 h, 37° C.), and prepared for 5'-end ligation in a pre-reaction volume of 47 µl containing: 1 µl 4 µl/µl T-hpa-24mer oligo, 1 µl 2 µg/µl dephosphorylated T-hpa-12mer oligo (FIG. 12), 5 µl ligase buffer and ddH$_2$O. Before 3 ml 5 U/µl $T_4$ ligase was added, the 47 µl mixture was heated to 50° C. (2 min), and gradually cooled down to 10° C. over a period of one hour, and then the ligation was performed at 14° C. (16 h). This formed the tester-amplicon. For subtracter-amplicon generation, 500 ng Hpa2-restricted control cDNAs were ligated to the S-hpa-12/24mer adaptors (FIG. 12) in the manner described above.

EXAMPLE 9

Covalence-modified Subtracter Generation

Uridine-analogs were incorporated into the subtracter sequences as described below. The subtracter-amplicon was diluted to 10 µg/ml, and four PCR reactions were set up on ice to generate subtracter uracil-incorporated DNA (U-DNA) for the control set. Each 50 µl reaction contained 2 µl diluted ligation, 1 µl 4 µg/µl S-hpa-24mer oligo primer, 2 µl dNTPs (10 mM dATP, 10 mM dCTP, 10 mM dGTP, and 30 mM dUTP), 5 µl 10 µl 10× PCR buffer, 1 µl 3.5 U/µl Taq DNA polymerase and ddH$_2$O. The S-hpa-12mer was melted away (5 min, 72° C.), and the empty ends were filled by Taq DNA polymerase (7 min, 72° C.). Twenty cycles of amplification were performed (1 min, 95° C.; 3 min, 72° C.), and the products were phenol-extracted, isopropanol-precipitated and resuspended in total 5 µl 10 mM Tris-buffer (Sambrook et. al., "*Molecular Cloning, 2nd Edition*", p10.49 (1989)). 80 µl 99% acetic anhydride was added (6 min, 98° C.) into the resuspended subtracter U-DNA to block amino-groups by acetylation which also made the subtracter become single-stranded. After the acetylated subtracter was recovered by Micropure™-EZ Enzyme Removers (Microcon-30) and resuspended in total 20 µl 10 mM Tris-buffer (pH 7.4), 40 µl 3M alkaline KMnO$_4$ was added (5 min, 98° C.; 1.5 hr, 72° C.) to generate carboxyl-groups on the $C_5/C_6$ of uracil/cytosine which can covalently bond to the amino-groups on the $C_6/C_2$ of adenine/guanine respectively. The carboxylated subtracter was finally recovered by Micropure™-EZ Enzyme Removers and resuspended in total 20 µl 10 mM alkaline N-[2-hydroxyethyl]piperiazine-N'-[3-propanesulfonic acid] (EPPS)/ethylenediaminetetraacetic acid (EDTA) buffer.

EXAMPLE 10

Subtractive Hybridization and Specific Amplification

The tester cDNA fragments were hybridized with covalence-modified subtracter fragments as described in the following example. For subtractive hybridization, 3 μg of T-adaptor-ligated tester-amplicon (testers) from non-treated cells was dissolved by 10 μl recovered-subtracter modified-DNA solution and denatured at 98° C. (5 min). The mixture was then cooled on ice (2 min), added with 2 μl 5M NaCl to adjust salt concentration, vortexed, overlaid mineral oil, and incubated at 68~70° C. (20 h). The hybridized-DNAs were diluted with 20 μl MgCl$_2$ solution (2.5 mM) and then two 50 μl PCR reactions were set up with: 2 μl diluted hybrids, 1 μl 4 μg/μl T-hpa-24mer oligo primer (FIG. 12), 2 μl dNTPs (10 mM dATP, 10 mM dCTP, 10 mM dGTP, and 10 mM dTTP), 5 μl 10× PCR buffer, 1 μl Taq/Pwo DNA polymerase mixture (3.5 U/μl) and 39 μl ddH$_2$O. The T-hpa-12mer was melted away (4 min, 72° C.), and ends were filled by Taq/Pwo DNA polymerase (6 min, 72° C.). Twenty cycles of PCR amplification were performed (1 min, 95° C.; 3 min, 72° C.), and the products were phenol-extracted, isopropanol-precipitated and resuspended in 20 μl 10 mM Tris buffer to give the final desired different sequences. Purification and recovery of the desired different sequences were accomplished by excising and eluting a 8% polyacryamide gel after electrophoresis (FIG. 11-A).

EXAMPLE 11

Cloning and Sequencing of Difference Products

The subtracted library was constructed as described below. Final difference products were cloned into the blunt site of a pCR2 vector using a Clontech TA Cloning kit. Then, the double-stranded circle vector was amplified in INVαF' cells (Invitrogen), prepared using a miniprep column (Qiagen), and sequenced with Sequenase v.2 DNA sequencing kit (Amersham) by dideoxy-mediated chain termination. Resulting sequences were searched and compared to the Genbank database using the BLAST program.

EXAMPLE 12

Northern Blot Hybridization

The successful isolation of differentially expressed genes was confirmed by Northern blot hybridization as described below. Total RNA (12 μg) isolated from both non-treated and activin-treated Y-79 cells was separated by electrophoresis through 1.0% agarose-formaldehyde gel and transferred to nylon filter (Schleicher & Schuell). The filter was dried and baked under UV-light (30 sec.) DNA probes from two PCR-amplified inserts (probe YC-1 and YC-2 in FIG. 11-A) were prepared with a Prime-It random labeling kit (Strategene) in the presence α-[$^{32}$-P] dATP. Northern blot hybridization was carried out for 5 hours at 68° C. in QuikHyb solution (Strategene). Blots were washed with 2% SSC, 0.1% SDS solution at room temperature twice (15 min each), followed by a 2 hour wash in 0.1% SSC, 0.1% SDS solution at 65° C.

As shown in FIG. 11-B, two specific mRNAs of approximately 3.7 and 6.6 kilobase were detected in the non-treated cells but much less in the activin-treated cells by YC-2 and YC-1, respectively.

EXAMPLE 13

Detection of Genomic Deletion in Retinoblastoma Cells

Y-79, a retinoblastoma cell, has been known to contain an RB-deletion in its genome. As a model of genomic subtraction by CHS, the genomic DNAs of normal retina cells and Y-79 cells were isolated by the IsoQuick nucleic acid extraction kit (Microprobe), restricted with Hpa2, and ligated to T-hpa-adaptor and S-hpa-adaptor respectively to give the tester (normal retina cell) and subtracter (Y-79). The size of restricted genomic DNA was about 1 kilobase which can be efficiently amplified by PCR. The uridine-analog was incorporated and covalently modified into subtracter as described in Example 9. The subtractive hybridization and selective amplification methods described in Example 10. were accomplished following by TA cloning and sequencing described in Example 11. The resulting subtracted tester DNA was shown in the FIG. 11-C. These cloned DNA fragments were then purified, random-prime labeled, and used to probe a Southern blot of genomic DNA fragments isolated from tester and subtracter respectively. A signal was detected on the normal DNA but not Y-79 DNA (FIG. 11-D). The sequencing result of this signal indicated a 108 base deletion in RB-exon 1.

Defined in detail, the present invention is a method of performing improved subtractive hybridization, comprising the steps of: (a) providing a first library of tester DNA, wherein said tester DNA is ligated to a tester-specific adaptor for primer-specific amplification; (b) contacting said tester DNA in denatured form with a second library of denatured subtracter DNA, wherein said subtracter DNA is single-stranded by amino-blocking agent and then covalent-modified by carboxylating agent in its base structures, to form a denatured mixture; (c) permitting said tester DNA and subtracter DNA in said denatured mixture to form double-stranded hybrid DNA comprising of hydrogen-bonded homoduplexes and covalently-bonded heteroduplexes; and (d) amplifying said hydrogen-bonded homoduplexes with tester-specific primer and thereby providing a library enriched in tester DNA that is not present in said library of subtracter DNA; (e) whereby said method provides a fast, simple and reliable isolation of desired different sequences from said two DNA libraries.

Alternatively defined in detail, the present invention is a kit for performing improved subtractive hybridization, comprising: (a) a specific tester-adaptor/primer which confers amplification-capability only to the tester DNA; (b) a specific subtracter-adaptor/primer which confers amplification-capability only to the subtracter DNA; (c) an amino-blocking agent which prevents the reassociation of the subtracter DNA; (d) a carboxylating agent which generates carboxyl-group on the base structures of the subtracter DNA; (e) a hybridization buffer which permits the tester and subtracter DNA in a denatured mixture to form hydrogen-bonded homoduplexes and covalently-bonded heteroduplexes; and (f) a specific amplification activity; (g) whereby said kit can be used to provide a fast, simple and reliable isolation of desired different sequences from said two DNA libraries.

Defined broadly, the present invention is a method of performing improved subtractive hybridization, comprising the steps of: (a) providing a first library of tester DNA, wherein said tester DNA is ligated to an adaptor for specific amplification; (b) contacting said tester DNA in denatured form with a second library of denatured subtracter DNA, wherein said subtracter DNA is denatured by hydrogen-bond-blocking agent and then modified by covalent-modifying agent in its nucleotide structures, to form a denatured mixture; (c) permitting said tester DNA and subtracter DNA in said denatured mixture to form hybrid duplexes comprising of hydrogen-bonded and covalently-bonded sequences; and (d) amplifying said hydrogen-bonded duplexes with said specific amplification and thereby providing a library enriched in tester DNA that is not present in said library of subtracter DNA; (e) whereby said method provides a fast, simple and reliable isolation of desired different sequences from said two DNA libraries.

Alternatively defined broadly, the present invention is a kit for performing improved subtractive hybridization, comprising: (a) a specific tester-adaptor/primer which confers amplification-capability only to the tester DNA; (b) a specific subtracter-adaptor/primer which confers amplification-capability only to the subtracter DNA; (c) a hydrogen-bond-blocking agent which makes the subtracter DNA single-stranded; (d) a covalent-modifying agent which generates covalent-bonding potentials on the structures of subtracter DNA in order to form covalent-bonding with the homologue of tester DNA; (e) a hybridization buffer which permits the tester and subtracter DNA in a denatured mixture to form hydrogen-bonded and covalently-bonded duplexes; and (f) a specific amplification activity; (g) whereby said kit can be used to provide a fast, simple and reliable isolation of desired different sequences from said two DNA libraries.

Defined more broadly, the present invention is a method of performing improved subtractive hybridization, comprising the steps of: (a) providing a first library of tester DNA, wherein said tester DNA can be specifically amplified; (b) contacting said tester DNA in denatured form with a second library of denatured subtracter DNA, wherein said subtracter DNA is modified by chemical agents to form covalent bonding with said tester DNA, to form a denatured mixture; (c) permitting said tester DNA and subtracter DNA in said denatured mixture to form hydrogen-binded and covalently-bonded hybrid sequences; and (d) amplifying said hydrogen-binded sequences and thereby providing a library enriched in tester DNA that is not present in said library of subtracter DNA; (e) whereby said method provides a fast, simple and reliable isolation of desired different sequences from said two DNA libraries.

Alternatively defined more broadly, the present invention is a kit for performing improved subtractive hybridization, comprising: (a) a specific tester-adaptor/primer which confers amplification-capability only to the tester DNA; (b) a specific subtracter-adaptor/primer which confers amplification-capability only to the subtracter DNA; (c) a first agent which makes the subtracter DNA single-stranded; (d) a second agent which makes subtracter DNA directly form covalent-bonding with the homologue of tester DNA; (e) a hybridization buffer which permits the tester and subtracter DNA in a denatured mixture to form hydrogen-binded and covalently-bonded hybrid sequences; and (f) an amplification activity; (g) whereby said kit can be used to provide a fast, simple and reliable isolation of desired different sequences from said two DNA libraries.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A method of performing improved subtractive hybridization, comprising the steps of:
   a) providing a first library of tester DNA, wherein said tester DNA is ligated to a tester-specific adaptor for primer-specific amplification;
   b) contacting said tester DNA in denatured form with a second library of denatured subtracter DNA, wherein said subtracter DNA has been rendered single-stranded by an amino-blocking agent and then covalent-modified by a carboxylating agent in its base structures, to form a denatured mixture;
   c) permitting said tester DNA and subtracter DNA in said denatured mixture to form double-stranded hybrid DNA comprising hydrogen-bonded homoduplexes and covalently-bonded heteroduplexes; and
   d) amplifying said hydrogen-bonded homoduplexes with tester-specific primer and thereby providing a library enriched in tester DNA that is not present in said library of subtracter DNA;
   whereby said method provides an isolation of desired different sequences from said two DNA libraries.

2. The method as defined in claim 1, further comprising the step of repeating steps (b) through (d) on said enriched library at least one time.

3. The method as defined in claim 1, further comprising the step of nucleotide-analog incorporation into said subtracter DNA between step (a) and step (b).

4. The method as defined in claim 3, wherein said nucleotide-analogs are incorporated into said subtracter DNA by DNA polymerase.

5. The method as defined in claim 4, wherein said DNA polymerase is Taq polymerase.

6. The method as defined in claim 1, wherein said primer-specific amplification is PCR amplification.

7. The method as defined in claim 1, wherein said amino-blocking agent is a chemical selected from the group consisting of acetic anhydride and alkaline acetic chloride.

8. The method as defined in claim 1, wherein said carboxylating agent is a chemical selected from the group consisting of potassium permanganate and sodium cyanide/sulfuric acid mixture.

9. The method as defined in claim 1, wherein said hydrogen-bonded homoduplexes and covalently-bonded heteroduplexes are formed by denaturation at approximately 90 to approximately 100° C. and then reassociation at approximately 60 to approximately 75° C.

10. The method as defined in claim 1, wherein said amplifying said hydrogen-bonded homoduplexes with tester-specific primer is completed by DNA polymerase.

11. The method as defined in claim 10, wherein said DNA polymerase is Taq polymerase.

12. The method as defined in claim 1, wherein said tester DNA and said modified subtracter DNA have a ratio of between about 1:1 and about 1:100.

13. The method as defined in claim 12, wherein said ratio is about 1:5 to 1:10.

14. A kit for performing improved subtractive hybridization, comprising:
   a) a specific tester-adaptor/primer which confers amplification-capability only to the tester DNA;
   b) a specific subtracter-adaptor/primer which confers amplification-capability only to the subtracter DNA;
   c) an amino-blocking agent which prevents the reassociation of the subtracter DNA;
   d) a carboxylating agent which generates carboxyl-group on the base structures of the subtracter DNA;
   e) a hybridization buffer which permits the tester and subtracter DNA in a denatured mixture to form hydrogen-bonded homoduplexes and covalently-bonded heteroduplexes; and
   f) an enzyme having DNA polymerase activity;
   whereby said kit can be used to provide an isolation of desired different sequences from said two DNA libraries.

15. The kit as defined in claim 14, further comprising a nucleotide analog for incorporation and modification into said subtracter DNA.

16. The kit as defined in claim 14, wherein said amino-blocking agent is acetic anhydride.

17. The kit as defined in claim 14, wherein said carboxylating agent is hot alkaline potassium permanganate.

18. The kit as defined in claim 14, wherein said hybridization buffer is alkaline EPPS/EDTA buffer.

19. The kit as defined in claim 14, wherein said DNA polymerase activity recited in (f) is Taq polymerase.

20. A method of performing improved subtractive hybridization, comprising the steps of:
   a) providing a first library of tester DNA, wherein said tester DNA is ligated to an adaptor for specific amplification;
   b) contacting said tester DNA in denatured form with a second library of denatured subtracter DNA, wherein said subtracter DNA is denatured by a hydrogen-bond-blocking agent and then modified by a base-oxidizing agent in its nucleotide structures, to form a denatured mixture;

c) permitting said tester DNA and subtracter DNA in said denatured mixture to form hybrid duplexes comprising hydrogen-bonded and covalently-bonded sequences; and d) amplifying said hydrogen-bonded duplexes with said specific amplification and thereby providing a library enriched in tester DNA that is not present in said library of subtracter DNA;

whereby said method provides an isolation of desired different sequences from said two DNA libraries.

21. The method as defined in claim 20, further comprising the step of repeating steps (b) through (d) on said enriched library at least one time.

22. The method as defined in claim 20, further comprising the step of nucleotide-analog incorporation into said subtracter DNA between step (a) and step (b).

23. The method as defined in claim 22, wherein said nucleotide-analogs are incorporated into said subtracter DNA by DNA polymerase.

24. The method as defined in claim 23, wherein said DNA polymerase is Taq polymerase.

25. The method as defined in claim 20, wherein said specific amplification is PCR amplification.

26. The method as defined in claim 20, wherein said hydrogen-bond-blocking agent is a chemical selected from the group consisting of acetic anhydride and alkaline acetic chloride.

27. The method as defined in claim 20, wherein said base-oxidizing agent is a chemical selected from the group consisting of potassium permanganate and sodium cyanide/sulfuric acid mixture.

28. The method as defined in claim 20, wherein said hybrid duplexes comprising hydrogen-bonded and covalently-bonded sequences are formed by denaturation at approximately 90 to approximately 100° C. and then reassociation at approximately 60 to approximately 75° C.

29. The method as defined in claim 20, wherein said amplifying said hydrogen-bonded duplexes with said specific amplification is completed by DNA polymerase.

30. The method as defined in claim 29, wherein said DNA polymerase is Taq polymerase.

31. The method as defined in claim 20, wherein said tester DNA and said subtracter DNA have a ratio of between about 1:1 and about 1:100.

32. The method as defined in claim 31, wherein said ratio is about 1:5 to 1:10.

33. A kit for performing improved subtractive hybridization, comprising:

a) a specific tester-adaptor/primer which confers amplification-capability only to the tester DNA;

b) a specific subtracter-adaptor/primer which confers amplification-capability only to the subtracter DNA;

c) a hydrogen-bond-blocking agent which makes the subtracter DNA single-stranded;

d) a base-oxidizing agent which generates oxidative groups on structures of subtracter DNA in order to form covalent-bonding with base structures of the tester DNA;

e) a hybridization buffer which permits the tester and subtracter DNA in a denatured mixture to form hydrogen-bonded and covalently-bonded duplexes; and f) an enzyme having DNA polymerase activity;

whereby said kit can be used to provide an isolation of desired different sequences from said two DNA libraries.

34. The kit as defined in claim 33, further comprising a nucleotide-analog for incorporation and modification into said subtracter DNA.

35. The kit as defined in claim 33, wherein said hydrogen-bond-blocking agent is acetic anhydride.

36. The kit as defined in claim 33, wherein said base-oxidizing agent is potassium permanganate.

37. The kit as defined in claim 33, wherein said hybridization buffer is EPPS/EDTA buffer.

38. The kit as defined in claim 33, wherein said DNA polymerase activity recited in (f) is Taq polymerase.

39. A method of performing improved subtractive hybridization, comprising the steps of:

a) providing a first library of tester DNA, wherein said tester DNA can be specifically amplified;

b) contacting said tester DNA in denatured form with a second library of denatured subtracter DNA, wherein said subtracter DNA is modified by chemical agents to form covalent bonding with said tester DNA, to form a denatured mixture;

c) permitting said tester DNA and subtracter DNA in said denatured mixture to form hydrogen-bonded and covalently-bonded hybrid sequences; and d) amplifying said hydrogen-bonded sequences and thereby providing a library enriched in tester DNA that is not present in said library of subtracter DNA;

whereby said method provides an isolation of desired different sequences from said two DNA libraries.

40. The method as defined in claim 39, further comprising the step of repeating steps (b) through (d) on said enriched library at least one time.

41. The method as defined in claim 39, further comprising the step of nucleotide-analog incorporation into said subtracter DNA between step (a) and step (b).

42. The method as defined in claim 41, wherein said nucleotide-analogs are incorporated into said subtracter DNA by DNA polymerase.

43. The method as defined in claim 42, wherein said DNA polymerase is Taq polymerase.

44. The method as defined in claim 39, wherein said specific amplification is PCR amplification.

45. The method as defined in claim 39, wherein said subtracter DNA is modified by a first agent and a second agent.

46. The method as defined in claim 45, wherein said first agent makes said subtracter DNA single-stranded.

47. The method as defined in claim 46, wherein said first agent is acetic anhydride or alkaline acetic chloride.

48. The method as defined in claim 45, wherein said second agent makes said subtracter capable of covalently bonding with said tester DNA.

49. The method as defined in claim 48, wherein said second agent is hot alkaline potassium permanganate or sodium cyanide/sulfuric acid mixture.

50. The method as defined in claim 39, wherein said hydrogen-bonded and covalently-bonded hybrid sequences are formed by denaturation at approximately 90 to approximately 100° C. and then reassociation at approximately 60 to approximately 75° C.

51. The method as defined in claim 39, wherein said amplifying said hydrogen-bonded sequences is completed by DNA polymerase with a specific primer.

52. The method as defined in claim 51, wherein said DNA polymerase is Taq polymerase.

53. The method as defined in claim 39, wherein said tester DNA and said subtracter DNA have a ratio of between about 1:1 and about 1:100.

54. The method as defined in claim 53, wherein said ratio is about 1:5 to 1:10.

55. A kit for performing improved subtractive hybridization, comprising:
   a) a specific tester-adaptor/primer which confers amplification-capability only to the tester DNA;
   b) a specific subtracter-adaptor/primer which confers amplification-capability only to the subtracter DNA;
   c) a first agent which makes the subtracter DNA single-stranded;
   d) a second agent which makes subtracter DNA directly form covalent-bonding with a homologue of tester DNA;
   e) a hybridization buffer which permits the tester and subtracter DNA in a denatured mixture to form hydrogen-bonded and covalently-bonded hybrid sequences; and
   f) an enzyme having DNA polymerase activity;
   whereby said kit can be used to provide an isolation of desired different sequences from said two DNA libraries.

56. The kit as defined in claim 55, further comprising a nucleotide-analog for incorporation and modification into said subtracter DNA.

57. The kit as defined in claim 55, wherein said first agent is acetic anhydride.

58. The kit as defined in claim 55, wherein said second agent is hot alkaline potassium permanganate.

59. The kit as defined in claim 55, wherein said hybridization buffer is EPPS/EDTA buffer.

60. The kit as defined in claim 55, wherein said DNA polymerase activity recited in (f) is Taq polymerase.

* * * * *